US007085351B2

(12) United States Patent
Lu et al.

(10) Patent No.: US 7,085,351 B2
(45) Date of Patent: Aug. 1, 2006

(54) METHOD AND APPARATUS FOR CONTROLLING ELECTRON BEAM CURRENT

(75) Inventors: Jianping Lu, Chapel Hill, NC (US); Otto Zhou, Chapel Hill, NC (US); Yuan Cheng, Chapel Hill, NC (US)

(73) Assignee: University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 10/358,160

(22) Filed: Feb. 5, 2003

(65) Prior Publication Data

US 2004/0028183 A1   Feb. 12, 2004

Related U.S. Application Data

(63) Continuation-in-part of application No. 09/679,303, filed on Oct. 6, 2000, now Pat. No. 6,553,096.

(51) Int. Cl.
*H01J 35/32* (2006.01)

(52) U.S. Cl. .................................. 378/122; 315/169.3

(58) Field of Classification Search ........ 378/127–129, 378/136, 109, 113, 122, 119; 315/169.3, 315/167, 168, 169.1, 112–118
See application file for complete search history.

(56) References Cited

U.S. PATENT DOCUMENTS

| | | | |
|---|---|---|---|
| 2,842,706 A * | 7/1958 | Dobischek et al. | 315/149 |
| 3,733,484 A | 5/1973 | Baynard | |
| 3,921,022 A | 11/1975 | Levine | |
| 4,253,221 A | 3/1981 | Cochran, Jr. et al. | |
| 5,129,850 A | 7/1992 | Kane et al. | |
| 5,138,237 A | 8/1992 | Kane et al. | |
| 5,616,368 A | 4/1997 | Jin et al. | |
| 5,623,180 A | 4/1997 | Jin et al. | |

(Continued)

FOREIGN PATENT DOCUMENTS

DE   197 00 992   7/1998

(Continued)

OTHER PUBLICATIONS

U.S. Appl. No. 09/296,572, filed Mar. 1, 1999, Bower et al.

(Continued)

*Primary Examiner*—David V. Bruce
*Assistant Examiner*—Hoon Song
(74) *Attorney, Agent, or Firm*—Jenkins, Wilson, Taylor & Hunt, P.A.

(57) ABSTRACT

An x-ray generating device includes a field emission cathode formed at least partially from a nanostructure-containing material having an emitted electron current density of at least 4 A/cm$^2$. High energy conversion efficiency and compact design are achieved due to easy focusing of cold cathode emitted electrons and dramatic reduction of heating at the anode. In addition, by pulsing the field between the cathode and the gate or anode and focusing the electron beams at different anode materials, pulsed x-ray radiation with varying energy can be generated from a single device. Methods and apparatus for independent control of electron emission current and x-ray energy in x-ray tubes are also provided. The independent control can be accomplished by adjusting the distance between the cathode and anode. The independent control can also be accomplished by adjusting the temperature of the cathode. The independent control can also be accomplished by optical excitation of the cathode. The cathode can include field emissive materials such as carbon nanotubes.

28 Claims, 20 Drawing Sheets

U.S. PATENT DOCUMENTS

| | | | |
|---|---|---|---|
| 5,637,950 | A | 6/1997 | Jin et al. |
| 5,648,699 | A | 7/1997 | Jin et al. |
| 5,726,524 | A | 3/1998 | Debe |
| 5,773,834 | A | 6/1998 | Yamamoto et al. |
| 5,773,921 | A | 6/1998 | Keesmann et al. |
| 5,844,963 | A * | 12/1998 | Koller et al. ............... 378/136 |
| 5,910,974 | A * | 6/1999 | Kuhn et al. ................ 378/138 |
| 5,973,444 | A | 10/1999 | Xu et al. |
| 5,976,444 | A | 11/1999 | Pearson et al. |
| 6,019,656 | A | 2/2000 | Park et al. |
| 6,057,637 | A | 5/2000 | Zettl et al. |
| 6,087,765 | A | 7/2000 | Coll et al. |
| 6,259,765 | B1 | 7/2001 | Baptist |
| 6,277,318 | B1 | 8/2001 | Bower et al. |
| 6,280,697 | B1 | 8/2001 | Zhou et al. |
| 6,333,968 | B1 | 12/2001 | Whitlock et al. |
| 6,334,939 | B1 | 1/2002 | Zhou et al. |
| 6,385,292 | B1 | 5/2002 | Dunham et al. |
| 6,440,761 | B1 | 8/2002 | Choi |
| 6,445,122 | B1 | 9/2002 | Chuang et al. |
| 6,456,691 | B1 * | 9/2002 | Takahashi et al. .......... 378/122 |
| 6,459,767 | B1 | 10/2002 | Boyer |
| 6,553,096 | B1 | 4/2003 | Zhou et al. |
| 2002/0110996 | A1 | 8/2002 | Yaniv et al. |
| 2002/0171357 | A1 | 11/2002 | Sun et al. |
| 2003/0002627 | A1 | 1/2003 | Espinosa et al. |

FOREIGN PATENT DOCUMENTS

| | | |
|---|---|---|
| WO | WO 00/51936 | 9/2000 |
| WO | 02/31857 A1 | 4/2002 |

OTHER PUBLICATIONS

U.S. Appl. No. 09/351,537, filed Jul. 1, 1999, Bower et al.
The X-Ray Tube (Radiologic Science for Technologist, S. C. Bushong, Mosby-Year Book, 1997 pp. 107-121).
C. Bower et al., "Fabrication and Field Emission Properties of Carbon Nanotube Cathodes", edited by Sullivan, J. Robertson, O. Zhou, T. Allen and B. Coll, *Mat. Res. Soc. Symp. Proc.*, vol. 593, pp. 215-220 (2000).
Y. Saito et al., "Field Emission Patterns from Single-Walled Carbon Nanotubes", *Jpn. J. Appl. Phys.*, vol. 36 (1997), pp. L1340-L1342, Part 2, No. 10A, Oct. 1, 1997.
Y. Saito et al., "Cathode Ray Tube Lighting Elements with Carbon Nanotube Field Emitters", *Jpn. J. Appl. Phys.*, vol. 37 (1998), pp. L346-L348., Part 2, No. 3B, Mar. 15, 1998.
W. Zhu et al., "Large Current Density from Carbon Nanotube Field Emitters", *Appl. Phys. Lett.*, American Institute of Physics, vol. 75, No. 6, Aug. 9, 1999, pp. 873-875.
Zhu et al., "Low-Field Electron Emission from Undoped Nanostructured Diamond," *Science*, vol. 282, 1471-1473 (Nov. 20, 1998).
Brodie et al., "Vacuum Microelectronics", *Advances in Electronics and Electron Physics*, edited by P.W. Hawkes, vol. 83, 1-106 (1992).
Okano et al., "Electron emission from nitrogen-doped pyramidal-shape diamond and its battery operation," *Appl. Phys. Lett.* 70 (16), 2201-2203 (Apr. 21, 1997).
Okano et al., "Fabrication of a diamond field emitter array," *Appl. Phys. Lett.*, 64 (20), 2742-2744 May 16, 1994.
Kumar et al., "Diamond-based field emission flat panel displays," *Solid State Technology*, vol. 38, 71-74 (May 1995).
Geis et al., "Diamond emitters fabrication and theory," *J. Vac. Sci. Technol. B*, 14(3), May/Jun. 1996, pp. 2060-2067.
Rinzler et al., "Unraveling Nanotubes: Field Emission from an Atomic Wire," *Science*, vol. 269, 1550-1553 (1995).
de Heer et al., "A Carbon Nanotube Field-Emission Electron Source," *Science*, vol. 270, 1179-1180 (Nov. 17, 1995).
Okazaki et al., "A New Emission Spectrum of $Au_2$ in the Gas Evaporation Technique: 761-809 nm," *Jpn. J. Appl. Phys.*, vol. 37, Pt. 1, 349, No. 1 (1998).
Wang et al., "Field emission from nanotube bundle emitters at low fields," *Appl. Phys. Lett.* 70(24), 3308-3310 (Jun. 16, 1997).
Yagishita et al., "Effects of Cleavage on Local Cross-Sectional Stress Distribution in Trench Isolation Structure," *Jpn. J. Appl. Phys.* 36, 1335-1340 (1997).
Wang et al., "A nanotube-based field-emission flat panel display," *Appl. Phys. Lett.* 72(2), 2912-2913 (Jun. 11, 1998).
Bonard et al., "Field emission from single-wall carbon nanotube films," *Appl. Phys. Lett.* 73(7), 918-920 (Aug. 17, 1998).
Thess et al., "Crystalline Ropes of Metallic Carbon Nanotubes," *Science* 273, 483-487 (Jul. 26, 1996).
Bower et al., "Synthesis and structure of pristine and alkali-metal-intercalated single-walled carbon nanotubes," *Appl. Phys.* A 67, 47-52 (1998).
Tang et al., "Electronic Structures of Single-Walled Carbon Nanotubes Determined by NMR," *Science*, vol. 288, 492-494 (Apr. 21, 2000).
Journet et al., "Large-scale production of single-walled carbon nanotubes by the electric-arc technique," *Nature*, vol. 388, 756-760 (Aug. 21, 1997).
Cassell et al., "Large Scale CVD Synthesis of Single-Walled Carbon Nanotubes," *J. Phys. Chem. B 103*, 6484-6492 (Jul. 20, 1999).
Chinese Office Action for Patent Application No. 01820211.X dated Nov. 18, 2005.

* cited by examiner

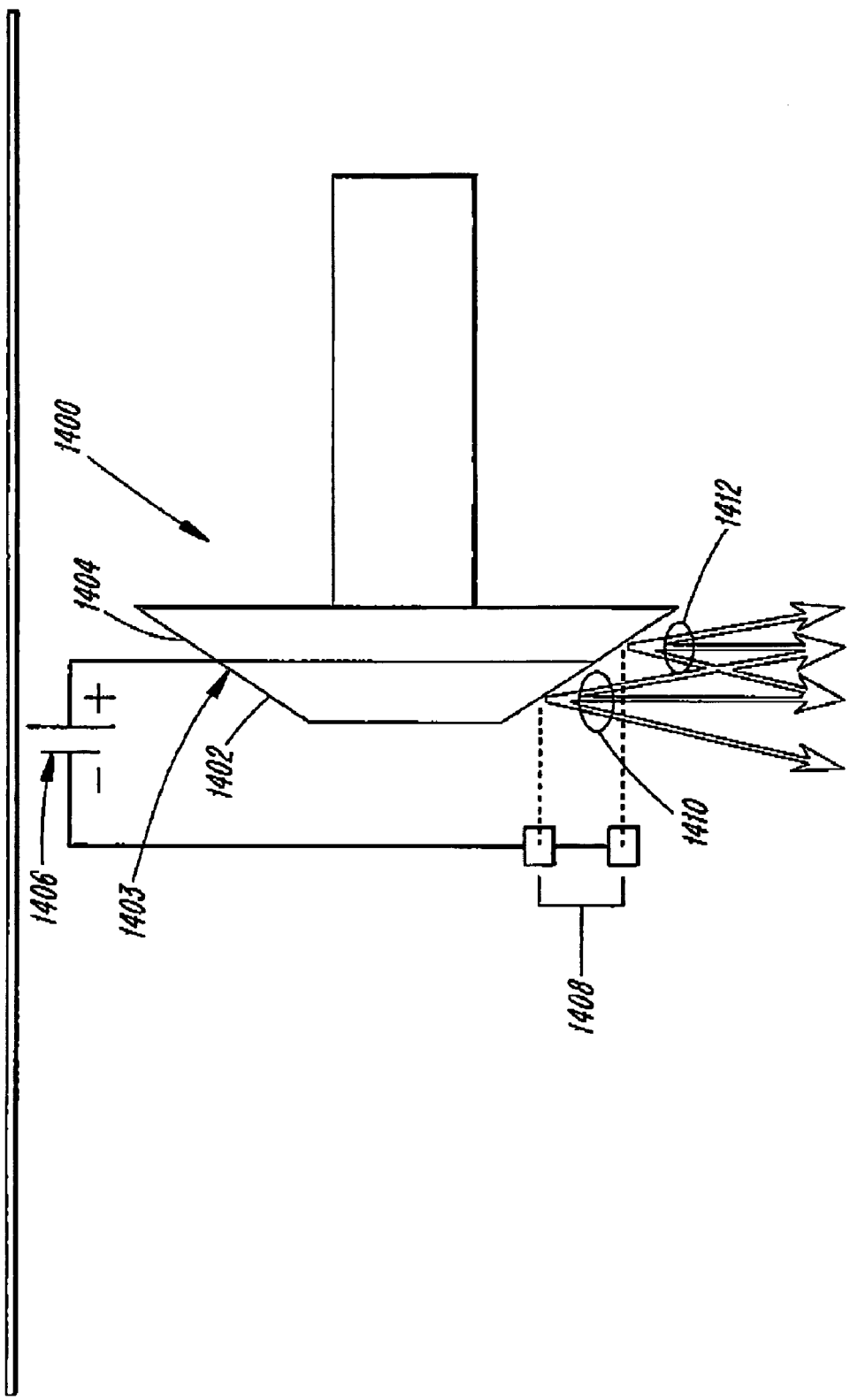

METHOD AND APPARATUS FOR CONTROLLING ELECTRON BEAM CURRENT

This application is a continuation-in-part of U.S. application Ser. No. 09/679,303, entitled "X-Ray Generating Mechanism Using Electron Field Emission Cathode," filed on Oct. 6, 2000 now U.S. Pat. No. 6,553,096, the entire contents of which are herein expressly incorporated by reference.

STATEMENT REGARDING FEDERALLY SPONSORED RESEARCH OR DEVELOPMENT

At least some aspects of this invention were made with Government support under the sponsorship of the Office of Naval Research, contract no. N00014-98-1-0597. The Government may have certain rights in this invention.

BACKGROUND OF THE INVENTION

In the description that follows, reference is made to certain structures and/or methods. However, the following references should not be construed as an admission that these structures and/or methods constitute prior art. Applicants expressly reserve the right to demonstrate that such structures and/or methods do not qualify as prior art against the present invention.

X-rays occupy that portion of the electromagnetic spectrum between approximately $10^{-8}$ and $10^{-12}$ m. Atoms emit x-rays through two separate processes when bombarded with energetic electrons.

In the first process, high-speed electrons are decelerated as they pass through matter. If an individual electron is abruptly decelerated, but not necessarily stopped, when passing through or near the nuclear field of a target atom, the electron will lose some of its energy which, through Plank's law, will be emitted as an x-ray photon. An electron may experience several such decelerations before it is finally stopped, emitting x-ray photons of widely different energies and wavelengths. This process produces the bulk of x-ray radiation and results in a continuous-type spectrum, also called Bremsstrahlung.

In the second process, an incident electron collides with and ejects an orbital electron of a target atom. If the ejected electron is from an inner shell orbit, then an electron in an outer shell orbit will fall to the inner vacant orbit with an attendant emission of an x-ray photon. In this process energy is emitted in the form of an x-ray whose energy or wavelength represents the orbital transition involved. Because the energies of orbital electrons are quantized, the x-ray photons emitted are also quantized and can only have discrete wavelengths characteristic of the atom. This gives rise to their classification as characteristic x-rays.

Several methods have been used to produce the incident electrons at a cathode and accelerate them into a target anode. One traditional approach has been the use of an x-ray tube. Depending upon the method used in generating the electrons, x-ray tubes may be classified in two general groups, gas tubes and high-vacuum tubes.

FIG. 1 shows a conventional gas x-ray tube. The x-ray generating device 110 is substantially made of a glass envelope 120 into which is disposed a cathode 125 which produces a beam of electrons 140 which strike an anode 130 thereby causing x-rays to be emitted 150 which can be used for sundry purposes including medical and scientific. The cathode is powered by a high voltage power supply via electrical leads 135. In addition, a gas pressure regulator 115 regulates the gas pressure in this type of x-ray device.

High vacuum tubes, an example of which is shown in FIG. 2, are a second type of x-ray tube. FIG. 2 shows a vacuum x-ray tube device with a thermionic cathode. In this type of device 210 a glass envelope 220 serves as the vacuum body. The cathode 225 is deposed within this vacuum and is provided with electrical leads 235. Electrons 240 are emitted by thermionic emission from the cathode 225 and strike an anode target 230 The efficiency of such emission of x-rays is very low causing the anode to be heated. To increase the lifetime of this device, it has been necessary to provide a cooling mechanism. One embodiment of a cooling mechanism is a chamber 260 through which water is circulated by the use of an inlet 265 and an outlet 270. To improve the efficiency of the emitted beam of electrons a focusing shield 245 is often utilized. The focusing shield 245 collimates the thermionically emitted electrons and directs them to the anode 230. However, the thermionic origin of the electrons makes focusing to a small spot size difficult. This, in part, limits the resolution of modern x-ray imaging (see, for example, Radiologic Science For Technologist, S. C. Bushong, Mosby-Year Book, 1997). X-rays 250 emitted from the anode 230 pass through a window 255 and are subsequently available for sundry purposes, including medical and scientific. An additional feature of this type of device is an exterior shutter 275. It has been found necessary to incorporate such a shutter to prevent the incidental emission of x-rays associated with the heating decay of the cathode. This is because even though the application of power to the cathode may be terminated, residual heating may be such that electrons continue to be emitted towards the target and continue to produce x-rays.

This process of x-ray generation is not very efficient since about 98 percent of the kinetic energy of the electron stream is converted upon impact with the anode into thermal energy. Thus, the focus spot temperature can be very high if the electron current is high or continuous exposure is required. In order to avoid damage to the anode it is essential to remove this heat as rapidly as possible. This can be done by introducing a rotating anode structure.

As noted above, a shutter (e.g. 275) is necessary in such devices because thermionic emission of electrons from a cathode does not allow for precise step function initiation and termination of the resulting electron beam. Indeed, while still at elevated temperatures and subsequent to removal of power, a thermionic cathode may emit electrons which may cause unwanted x-ray emission from the target. In operation the shutter is held open either mechanically or by means of a microswitch.

Moreover, due to high temperature heating, the cathode filament has a limited lifetime, typically around a few hundred hours in medical applications and thousand hours in analytical applications. Under normal usage, the principle factor determining the lifetime of the x-ray tube is often damage to the cathode filament.

The amount of useful x-rays generated in the anode is proportional to the electron beam current striking at the anode. In thermionic emission, the electron beam current is only a small fraction of the current passing through the cathode filament (typically 1/20). In modern medical applications such as digital radiography and Computed Tomography (CT), very high x-ray intensity is required concomitantly requiring a very high thermionic emission cathode current. Therefore, a principle limitation in these applications is the amount of electron beam current generated by the cathode.

A possible improvement in the generation of x-rays is the introduction of field emission cathode materials. Field emission is the emission of electrons under the influence of a strong electric field. However, the incorporation of conventional field emission cathode materials into x-ray generating devices presents certain challenges. For instance, the field emission cathode materials must be capable of generating an emitted electron current density of a sufficiently high level (can be as high as 2000 mA on the target for medical applications) such that, upon striking the anode target material, the desired x-ray intensity is produced.

Many conventional field emission materials are incapable of producing the desired emitted electron circuit density absent the application of a relatively high electrical field to the cathode. Moreover, many of the conventional field emission materials cannot produce stable emissions at high current densities under high applied electrical fields. The use of high control voltages increases the likelihood of damaging the cathode material, and requires the use of high powered devices which are costly to procure and operate.

Conventional field emission materials such as metals (such as Mo) or a semiconducting materials (such as Si), with sharp tips in nanometer sizes have been utilized. Although useful emission characteristics have been demonstrated for these materials, the turn-on electric field is relatively high, typically on the order of 50–100 V/µm at a current density of 10 mA/cm$^2$. (See, for example, W. Zhu et al., *Science*, Vol. 282, 1471, (1998)).

Carbon materials, in the form of diamond and carbon nanotubes, have emerged as potentially useful for electron field emission materials.

Low-field emission has been observed in diamond-based materials (3–5 V/µm for 10 mA/cm$^2$ current density). However, the emission is unstable above a current density of 30 mA/cm$^2$ and the fabrication of uniform sharp tips is difficult and costly. Moreover, the stability of these materials in a real device environment is of concern, partially due to ion bombardment, reaction with chemically active species and high temperatures. (See, for example, I. Brodie and C. A. Spindt, "Advances in Electronics and Electron Physics", edited by P. W. Hawkes, Vol. 83, 1 (1992)).

The use of diamond materials as field emitters also suffers from the problem that the diamond produces lower than desired current densities. While observations of localized emission hot spots have been reported as having a current density on the order of 100 A/cm$^2$, the actual emission areas have not been measured, neither are they understood or reproducible. See, e.g. K. Okano et al., *Applied Physics Letters*, Vol. 70, 2201 (1997), which is hereby incorporated by reference in its entirety. Diamond emitters and related emission devices are disclosed, for example, in U.S. Pat. Nos. 5,129,850; 5,138,237; 5,616,368; 5,623,180; 5,637,950; 5,648,699; Okano et al., *Applied Physics Letters*, Vol. 64, 2742 (1994); Kumar et al., *Solid State Technologies*, Vol. 38, 71 (1995); and Geis et al., *Journal of Vacuum Science Technology*, Vol. B14, 2060 (1996), all of which are hereby incorporated by reference in their entirety.

The previously published studies of carbon nanotube emission materials have reported relatively low current densities, typically on the order of 0.1–100 mA/cm$^2$. The higher reported electron emission data are difficult to interpret and are unreliable because, for example, the data is independent of the distance between the emitting cathode and target anode material (U.S. Pat. No. 6,057,637). Carbon nanotube emitters are disclosed, for example, in T. Keesmann in German Patent No. 4,405,768; Rinzler et al., *Science*, Vol. 269, 1550 (1995); De Heer et al., *Science*, Vol. 270, 1179 (1995); Saito et al., *Japan Journal of Applied Physics*, Vol. 37, 1. 346 (1998); Wang et al., *Applied Physics Letters*, Vol. 70, 3308 (1997); Saito et al., *Japan Journal of Applied Physics*, Vol. 36, 1. 1340 (1997); Wang et al., *Applied Physics Letters*, Vol. 72, 2912 (1998); and Bonard et al., *Applied Physics Letters*, Vol. 73, Page 918 (1998), all of which are hereby incorporated by reference in their entirety.

Emissions as high as 4 A/cm$^2$ from single-wall carbon nanotube films deposited on different substrates has been reported (W. Zhu et al., *Applied Physics Letters*, Vol. 75, 873 (1999), pending U.S. patent application Ser. No. 09/259, 307). The threshold field for 10 mA/cm$^2$ current density is <5 V/µm (C. Bower et al., in "Amorphous and Nanostructured Carbon", edited by J. Sullivan, J. Robertson, O. Zhou, T. Allen, and B. Coll, *Materials Research Society Symposium Proceeding*, Vol. 593, Page 215 (2000)).

X-ray tubes used for medical applications usually contain dual focus spots with "apparent" spot sizes of 0.3 mm$^2$ and 1 mm$^2$. With a target angle of 6° and 15°, this corresponds to an actual area of electron bombardment of 0.3×3 mm$^2$ and 1×4 mm$^2$. Further reduction of the focus spot requires a smaller target angle and a higher electron current. This is not possible due to constraints of power supplied to the cathode filament.

Another difficulty with a conventional thermionic emitter is the space charge effect. The space charge is very sensitive to applied x-ray voltage (kV) and filament current. Thus, it is difficult to achieve independent control of electron beam current (mA) and kV unless the tube is operating in the so called saturation limit. This generally implies larger mA for higher kV.

In digital fluoroscopy and radiography, an energy subtraction technique (where the image obtained with a lower average x-ray energy is subtracted from that produced by a higher x-ray energy) is used to enhance the contrast of certain materials (such as contrasting agent iodine). See, for example, Radiologic Science for Technologist, S. C. Bushong, Mosby-Year Book, 1997. This requires alternating high and low kV in every data point acquired. Due to the inherent difficulty of initiation and termination of thermionic electron sources, the process is slow and patients are exposed to unnecessary higher dosages of x-rays.

In computed tomography, the uniformity of the x-ray fan beam is crucial. Achieving uniformity in conventional tube design is difficult because emission of x-rays from the target surface is anisotropic (namely, dependent on the emission direction relative to the surface). Different parts of the x-ray beam come from different combinations of emission angles from different parts of the focus area. Thus, even when the focus spot is bombarded with a uniform electron beam the resulting x-ray beam is non-uniform.

Therefore, it would be desirable to construct x-ray generating devices which incorporate field emitting cathode materials capable of reliably producing high emitted electron current densities, without reliance upon thermionic emissions, or high control or externally applied voltages. It would also be desirable to provide x-ray generating devices with an emitted electron beam that is easy to control and focus.

In many applications, such as in medical diagnostics and treatments, it is desirable to have independent controls on the electron emission current (mA) and the x-ray energy (kVp). However, conventionally the emission current from a field emission cathode is controlled by varying the voltage between the cathode and anode in a diode structure, or in the case of a triode structure, between the electron emission surface and the gate structure in the cathode. Varying the voltage will change the electron kinetic energy bombarding the x-ray generating target materials. Since the x-ray energy is determined by the electron kinetic energy, the resulting x-ray will have different energies. However, these conventional methods do not allow for independent controls of the electron emission current and the x-ray energy. Accordingly, it would be desirable to independently control the electron emission current and the x-ray energy.

SUMMARY OF THE INVENTION

The present invention avoids the undesirable features of current x-ray generating devices by incorporating a field emission nanostructure cathode material into an x-ray generating device. The nanostructure field emission material of the present invention is capable of producing, in a controlled and reliable manner, a high emitted electron current density through the application of a relatively small control electrical field. Therefore, a substantially higher electron beam current can be achieved compared with that of thermionic emission. The nanostructure field emission cathode of the present invention is capable of providing precise step-function initiation and termination of the emission of electrons in a pulse of varying duration simply by varying the applied voltage. The problem of residual emission during thermal decay experienced in thermionic emission is avoided. Using x-ray tubes with nanostructure based field-emission cathodes of the present invention, it is also possible to construct portable x-ray machines for use in the field.

In addition to being advantageously pulsed, field emission electrons may be directed to particular areas on the anode target region by the use of either mechanical and/or electrical means that control the orientation of the beam within the x-ray generating device. The orientation feature allows for the use of multiple anode target materials within one x-ray device, thus generating a larger range of characteristic x-rays in a single device. Additionally, the reduced bombardment time on the anode results in a lower anode cooling requirement with attendant reduction in device peripherals.

The use of a nanostructure cathode material enables the emission of a high electron beam current which is stable and easy to control and focus. Thus, x-ray generating devices of the present invention provide for a variety of medical applications that make capable dramatic improvements in imaging quality and speed over current designs. The main characteristics required of x-ray beams for medical applications are high intensity, precise control of x-ray generation, and small "apparent" focus spot.

With a nanostructure field emitter, the electron beam current is the same as that supplied to the cathode. Thus, there is no difficulty in achieving an order of magnitude higher electron beam current. The present invention provides new designs of anode targets with substantially smaller angles, hence smaller "apparent" focus spot sizes. This can lead to dramatic enhancements of imaging resolution and speed. For example, dual focus spots of 0.1 mm$^2$ and 0.3 mm$^2$ with a target angle of 2° and 6° are envisioned. Thus, devices of the present invention would be able to produce the same amount of x-ray as in current machines but with a 3–4 times better resolution, or comparable resolution but with 3–4 times more intensive x-ray beam.

In the case of nanostructure electron field emitters, the space charge limit is not reached at the current density required for x-ray tubes. Thus, independent and stable control of mA and kV is possible with x-ray device designs of the present invention.

By the present invention, rapid pulsation of the field emitter can be readily achieved leading to dramatic speed up of digital imaging in fluoroscopy, radiography, and tomography thereby reducing patient's exposure to unnecessary radiation.

Due to the easy control and focusing of the electron beam from a field emitter, according to the present invention, an anode with multiple target materials can be achieved. For example, the aforementioned pulsation of x-ray energy can be generated by focusing the same electron beam alternatively at high Z (which produces higher average x-ray energy) and low Z (producing lower average x-ray energy) materials without changing the kV applied between anode and cathode. Such a technique simplifies the power supply structure, hence reducing the associated cost. This design of anode targets and field emitters will enable pulsation of different x-ray energy without pulsation of the kV, thus reducing the cost and enhance the speed in digital imaging such as fluoroscopy, radiography, and computed tomography.

With a field emitter according to the present invention and its associated ease of control, it is possible to engineer a distributed electron beam such that it compensates for the anisotropic effect. Thus, the x-ray design with a field emitter will enable production of a superior uniform x-ray beam, thus enhancing the contrast and resolution in digital imaging.

According to a first aspect, an x-ray generating device is provided comprising: a chamber; a field emission cathode the cathode comprising a nanostructure-containing material having an emitted electron current density of more than A/cm$^2$; an anode target; and an accelerating field established by an applied potential between the cathode and anode.

According to a further aspect, a method of generating x-rays comprises: providing a chamber; introducing a field emission cathode into the chamber, the cathode comprising a nanostructure-containing material having an emitted electron current density of more than 4 A/cm$^2$; applying a control voltage to the cathode thereby causing a stream of electrons to be emitted; and providing an anode target within the chamber incident to the stream of emitted electronics thereby causing x-rays to be emitted from the anode target.

According to the present invention, both the current density and its distribution can be precisely controlled by an applied or control voltage.

The present invention provides methods and apparatus for controlling electron beam current. Specifically, the present invention allows independent control of the electron emission current and the x-ray energy. In accordance with the exemplary embodiments of the present invention, the cathode is coated with electron field emission materials, such as carbon nanotubes. Moreover, in exemplary embodiments of the present invention, the cathode and anode are disposed in a vacuum tube.

In accordance with a first embodiment of the present invention, independent control of the electron emission current and the x-ray energy is achieved by adjusting the distance between the cathode and anode. In accordance with one aspect of this embodiment, the distance is adjusted by varying an amount of electricity applied to a piezoelectric material which is attached to the cathode and/or the anode. In accordance with another aspect of this embodiment, the cathode and/or anode is mounted on a mechanically adjustable platform.

In accordance with a second embodiment of the present invention, independent control of the electron emission current and the x-ray energy is achieved by adjusting the temperature of the cathode.

In accordance with a third embodiment of the present invention, independent control of the electron emission current and the x-ray energy is achieved by shining an optical light source on the cathode. Specifically, the optical light source, for example a photon source, emits protons on the field emissive material of the cathode to adjust the carrier density and temperature of the field emissive materials. In accordance with one aspect of this embodiment, the cathode comprises multiple emitters which are selectively bombarded by the optical light source.

BRIEF DESCRIPTION OF THE DRAWING FIGURES

Objects and advantages of the invention will become apparent from the following detailed description of preferred embodiments thereof in connection with accompanying drawings in which like numerals designate like elements and in which:

FIG. 14 is a schematic illustration of a multiple target rotatable anode of the present invention.

FIGS. 15*a*–15*d* illustrate an exemplary x-ray tube in accordance with a first embodiment of the present invention.

Figure 16A:
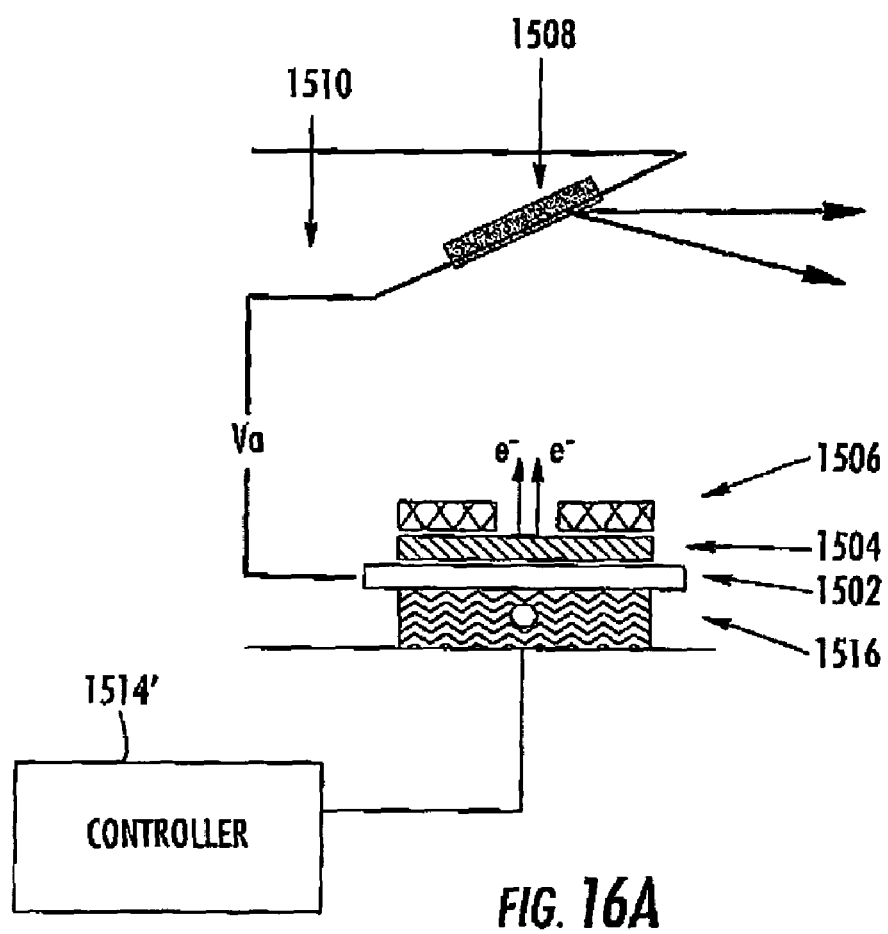
Figure 16B:
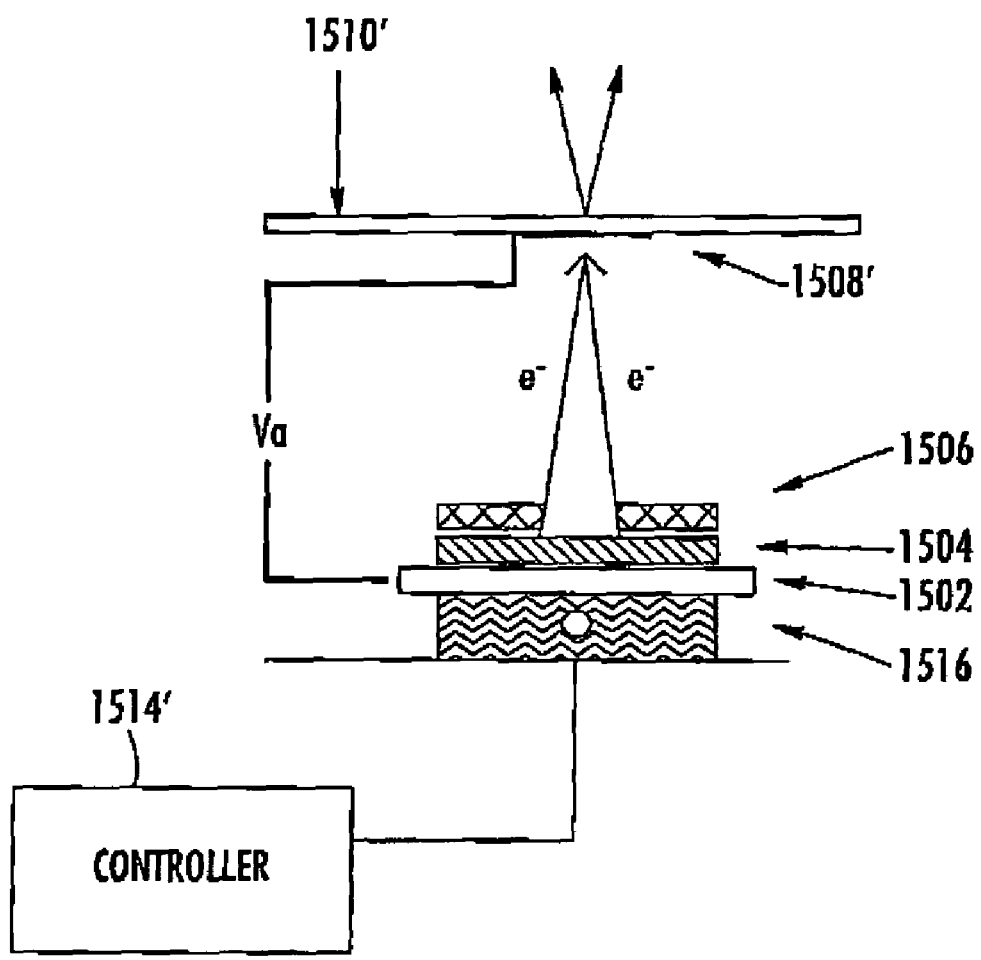

FIGS. 16*a* and 16*b* illustrate an exemplary x-ray tube in accordance with a second embodiment of the present invention.

Figure 17:
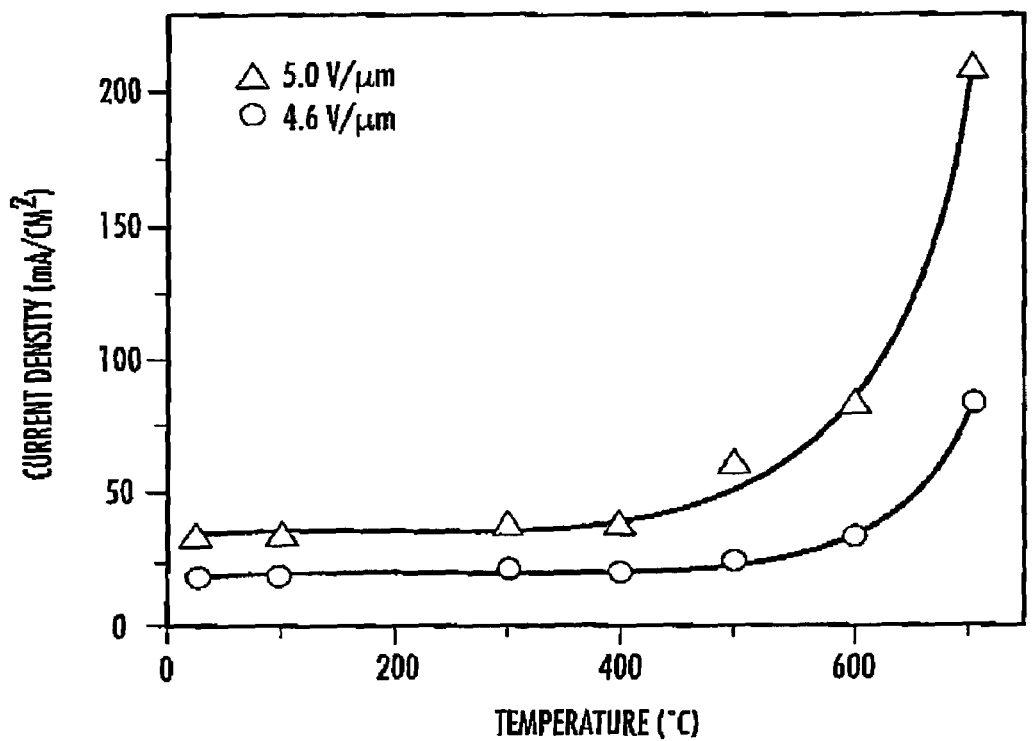

FIG. 17 illustrates the measured electron emission current as a function of temperature under two different applied electric fields in accordance with exemplary embodiments of the present invention.

Figure 18A:
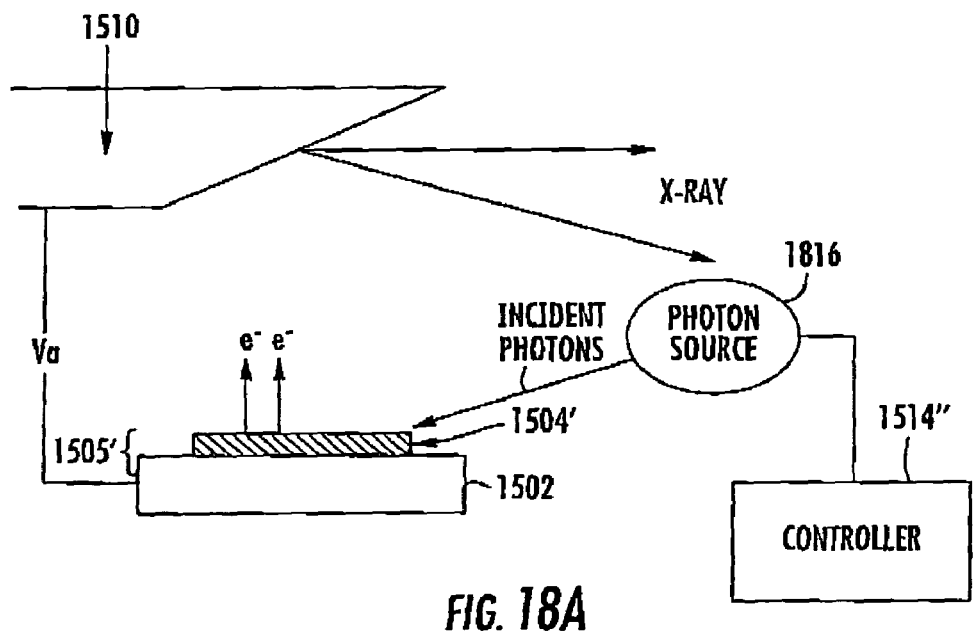
Figure 18B:
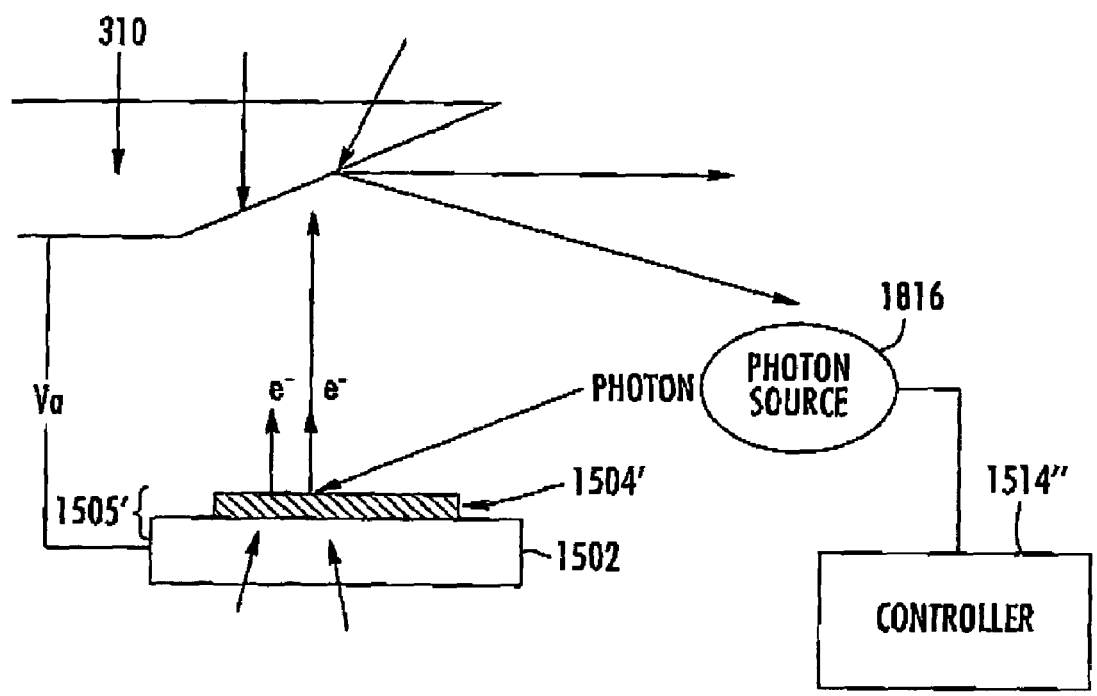
Figure 18C:
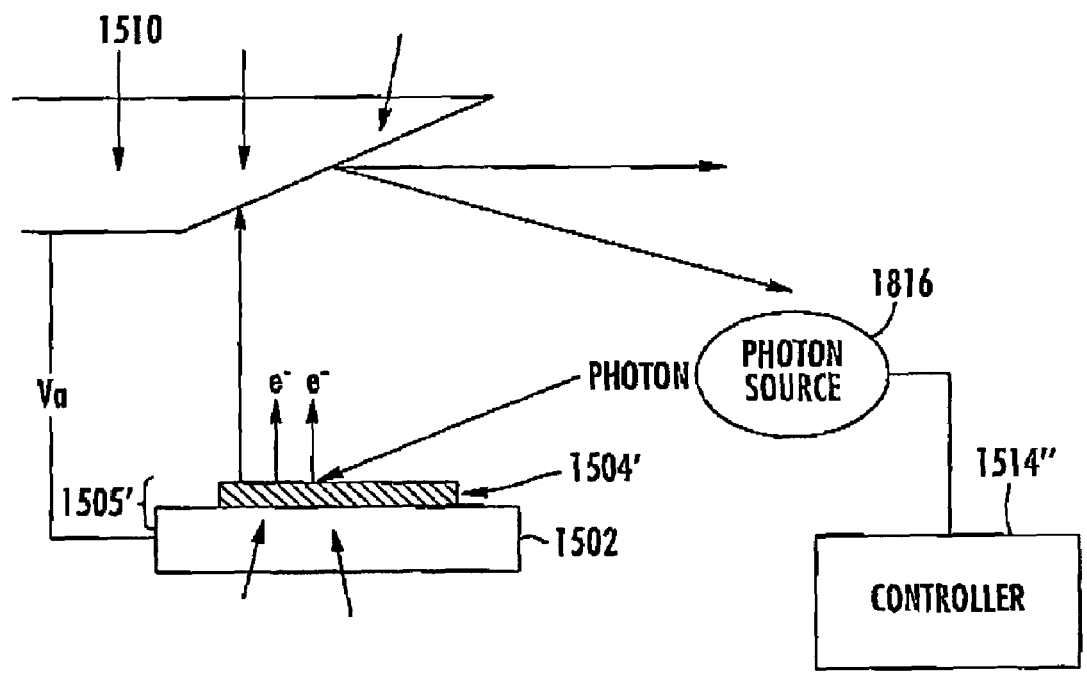

FIGS. 18*a*–18*c* illustrate an exemplary x-ray tube in accordance with a third embodiment of the present invention.

DETAILED DESCRIPTION OF THE INVENTION

In the following description, for the purposes of explanation and not limitation, specific details are set forth in order to provide a thorough understanding of the present invention. However, it will be apparent to one skilled in the art that the present invention may be practiced in other embodiments that depart from these specific details. In other instances, detailed descriptions of well know methods, devices, and circuits are omitted so as not to obscure the description of the present invention.

According to the present invention, a cathode of an x-ray generating device is formed, at least in part, by a nanostructure-containing material. Nanostructure materials have nanometer scale dimensions. These nanostructures can have various shapes, such as spherical, rod/wire-shaped, or tubular.

Numerous nanostructure materials, which possess high emission current densities, are contemplated by the present invention. For example, nanostructure containing materials formed from silicon (Si), germanium (ge), aluminum (Al), silicon oxide, germanium oxide, silicon carbide, boron, boron nitride, and boron carbide are contemplated. More specific details of the above-mentioned materials can be gleaned from U.S. Pat. No. 6,334,939, (Ser. No. 09/594,844), the disclosure of which is incorporated herein by reference, in its entirety.

According to a further embodiment of the present invention, the materials used to form at least part of a cathode in an x-ray generating device comprise carbon nanotubes, either single wall nanotubes or multi wall nanotubes.

The cathode may be formed in any suitable manner. For instance, it is known to form field emitting cathodes with various geometrical configurations, such as one or more sharp points or ridges which act to focus the beam of emitted electrons. See, for example, U.S. Pat. No. 3,921,022 to Levine; U.S. Pat. No. 4,253,221 to Cochran Jr., et al.; and U.S. Pat. No. 5,773,921 to Keesmann et al., the disclosures of which are incorporated herein by reference.

The cathode may be formed entirely of the nanotube material of the present invention, or may comprise a substrate that is at least partially coated with a nanotube material.

Numerous single wall nanotube fabrication techniques are envisioned. For example, the single wall nanotubes can be fabricated using a laser ablation process. This technique is generally described, for example, in A. Thess et al., *Science;* 273, 483–487 (1996); C. Bower et al., *Applied Physics*, Vol. A67, 47 (1998); X. P. Tang et al. *Science*, Vol. 288, 492 (2000), the disclosure of which are hereby incorporated by reference. Single wall carbon nanotubes can also be fabricated by arc-discharge (See, for example, C. Journet et al., Nature, Vol. 388, 756 (1997)) and chemical vapor deposition (See, for example, A. M. Cassell et al. *J. of Physical Chemistry B,* 103, 6484 (1999)) techniques.

One particularly suitable technique of forming single wall nanotubes according to the present invention includes a technique as described in U.S. Pat. No. 6,280,307 (Ser. No. 09/259,307) the disclosure of which is incorporated herein by reference, in its entirety.

According to an exemplary technique, a target made from graphite and a suitable catalyst, such as nickel and/or cobalt is placed within a quartz tube. The target is formed from a graphite powder mixed with 0.6 atomic percent nickel and 0.6 atomic percent cobalt, and graphite cement. The target is then heated within the tube to a temperature of approximately 1150 C. The tube is evacuated by means of a vacuum pump and a flow of inert gas, such as argon, is introduced into the tube by a suitable source. Various control devices may be attached to the system for controlling and monitoring the flow of inert gas into the tube, as well as the vacuum within the tube. The pressure of the inert gas as is maintained at a suitable level, such as approximately 800 torr.

An energy source, such as a pulsed Nd:YAG laser, is used to ablate the target at the above-described temperature. Preferably, the first and/or second harmonic beam of the laser, i.e., 1064 nm and 532 nm, respectively, are used to ablate the target.

As the target is ablated, nanotube-containing material is transported downstream by the inert gas flow, and forms deposits on the inner wall of the tube. These deposits are then removed to recover the nanotube-containing material. This material, as recovered, has been analyzed and found to contain 50–70 volume % of SWNTs with individual tube diameters of 1.3–1.6 nm and bundle diameters of 10–40 nm. The bundles are randomly oriented.

The as-recovered materials are then purified by a suitable purification process. In a preferred embodiment, the nanotube material is placed in a suitable liquid medium, such as an organic solvent, preferably an alcohol such as methanol. The nanotubes are kept in suspension within the liquid medium for several hours using a high powered ultrasonic horn, while the suspension is passed through a micro porous membrane. In another embodiment, the carbon nanotube containing material is first purified by reflux in a suitable solvent, preferably 20% $H_2O_2$ with subsequent rinsing in $CS_2$ and then in methanol, followed by filtration, as described in Tang et al. Science, Vol. 288, 492 (2000).

Although not limiting the present invention to any particular theory, it is contemplated that a nanotube material produced according to the above-described process of the present invention enhances the ability of the material to emit electrons. Moreover, it is believed that the above-described synthesized SWNTs have a very low electrical resistance. It is believed that the above-described features imparted to the single wall nanotube material of the present invention enable the material to outperform, in a more reliable and consistent manner, previously investigated materials.

In addition to the above described processing steps, the purified materials can be further processed by milling, such as ball-milling or oxidation. The optional step of milling will of course act to create even more broken nanotubes and theoretically at least even further increase the number of ends of the nanotubes which are capable of forming sites for the emission of electrons toward an anode target. The carbon nanotubes can also be shortened by oxidation in strong acid. The length of the nanotubes can be controlled by the acid concentration and reaction time. In a preferred embodiment, the purified single wall carbon nanotubes are sonicated in a solution of 3:1 volume ratio of $H_2SO_4$ and $HNO_3$. The average nanotube length is reduced to 0.5 micron (from 10–30 micron in the as purified case) after 24 hours of sonication. More emission tips per unit area can be obtained using the short nanotubes.

The above-described nanostructure materials, such as a purified single wall nanotube material can be deposited as a film on a cathode substrate material. An important advantage of the materials of the present invention is that they can be deposited on a substrate, or otherwise formal as a film, without resorting to the use of binder materials. The use of binder materials adversely affects the electrical properties of the material, thereby negatively impacting its field emission characteristics.

Figure 1:
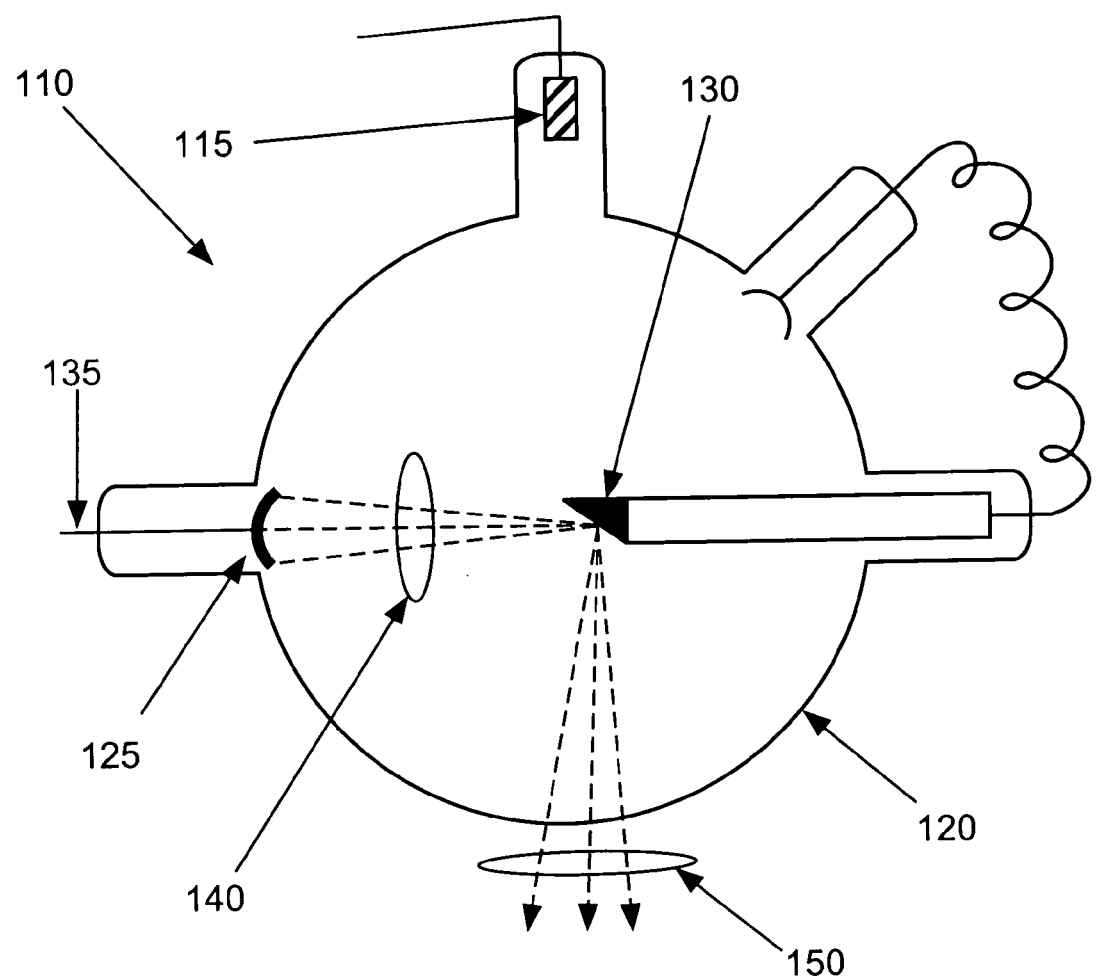
FIG. 1 is a cross-section of a conventional gas x-ray tube.
Figure 2:
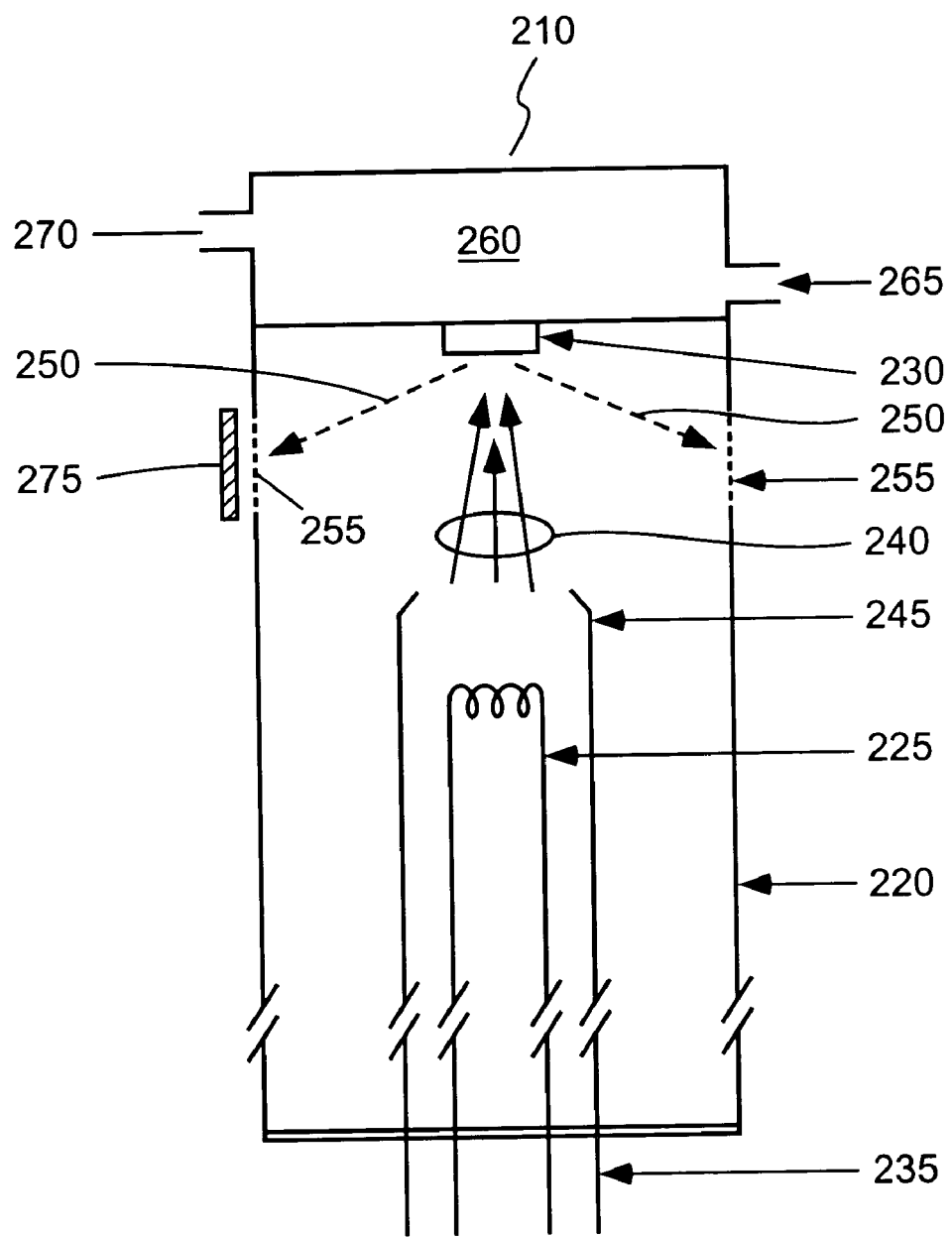
FIG. 2 is a cross-section of a conventional vacuum x-ray tube.
Figure 3:
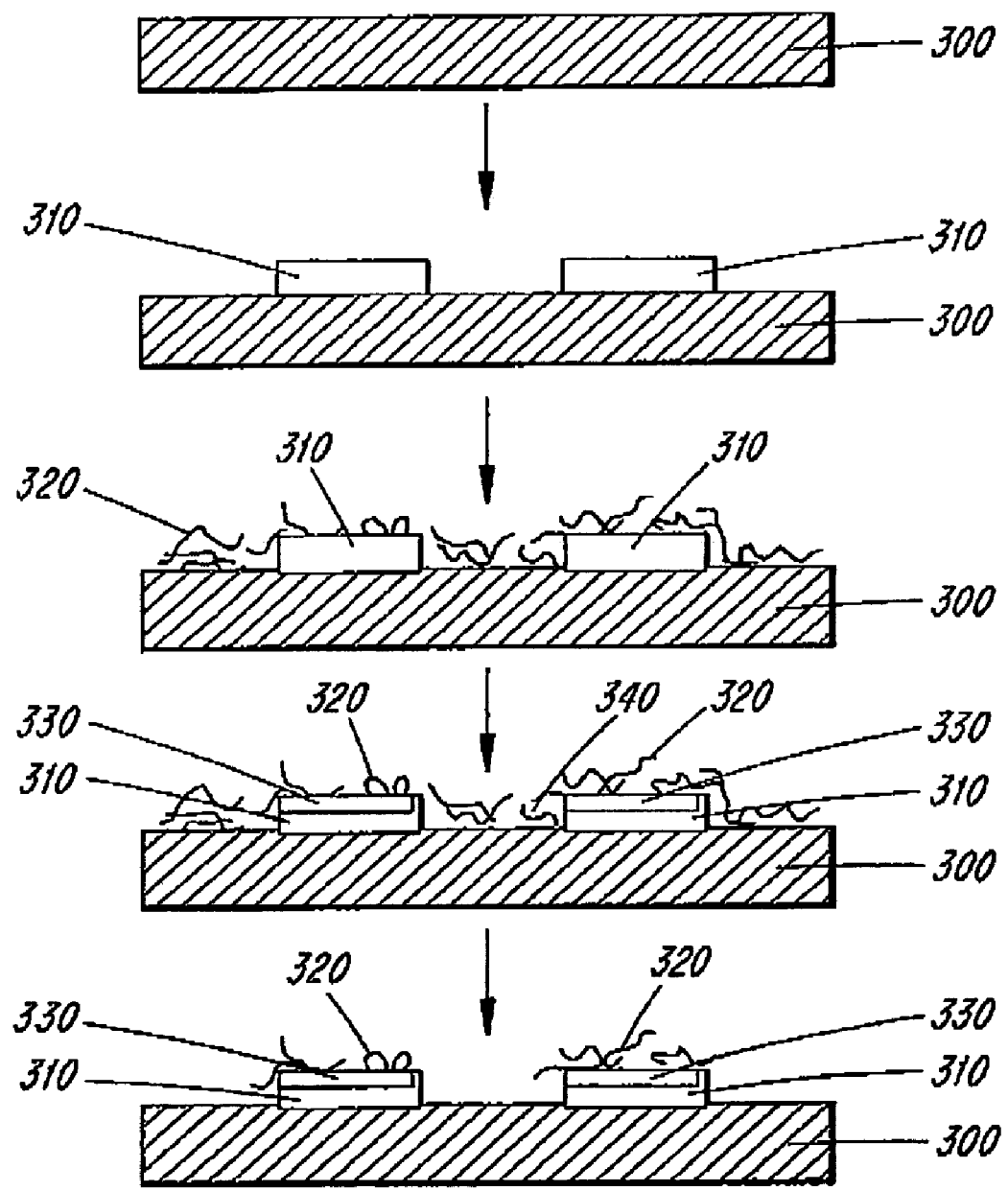
FIG. 3 is a process diagram depicting the major steps in the fabrication of single wall carbon nanotubes into field emission cathodes.

FIG. 3 depicts schematically the major steps in an exemplary technique for depositing and preparing a field emission cathode. A substrate 300 is provided, the particular cathode substrate material utilized is not especially critical, and may comprise any suitable conventionally used electrically conducting materials. Preferably, a thin, carbon-dissolving or carbide-forming metal interlayer 310 is deposited on the substrate before applying the nanostructure materials, e.g., single wall carbon nanotubes 320. An example of the carbon-dissolving or carbide-forming metal interlayer 310 materials includes Ni, Fe, Co, Mn, Si, Mo, Ti, Ta, W, Nb, Zn, V, Cr and Hf. A film 330 is then formed by annealing, followed optionally by sonification to remove excess SWNTs 340 from the device. Annealing is conducted under high vacuum, preferably under $10^{-6}$ torr, at a temperature where a thin carbide layer can be formed at the metal interlayer and carbon nanotube, or suitable nanostructure, interface or where a small amount of carbon can be dissolved. After such treatment, the carbon nanotubes or suitable nanostructure become adherent on the substrate.

Figure 6:
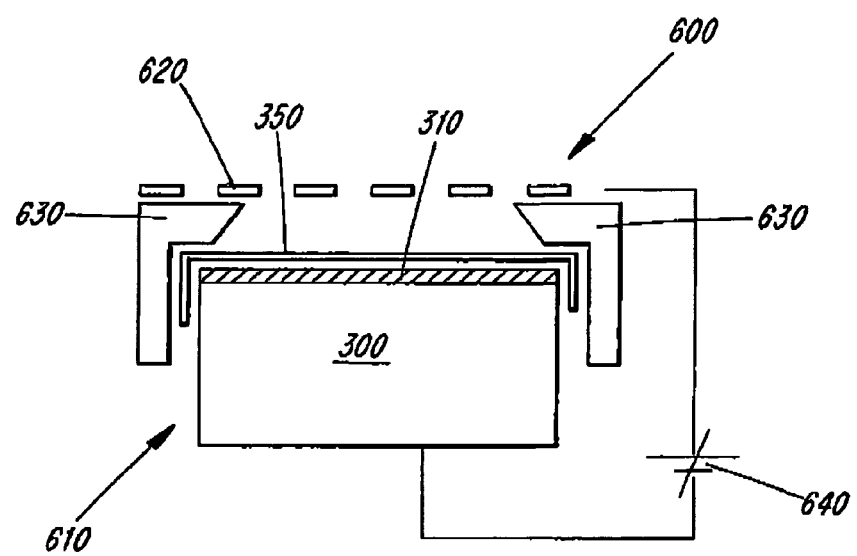
FIG. 6 is a cross-section of a carbon nanotube field emission device according to another embodiment of the invention.
Figure 7A:
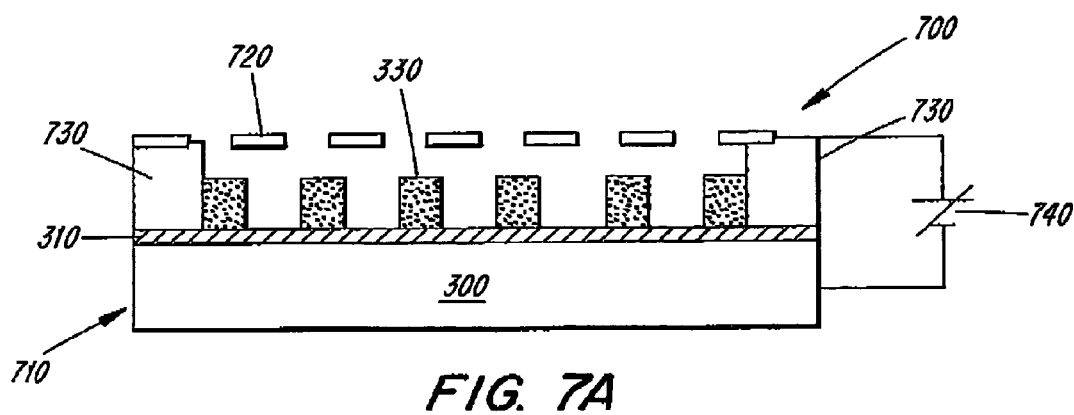
FIG. 7A is a cross-section of a carbon nanotube field emission device according to yet another embodiment of the invention.
Figure 7B:
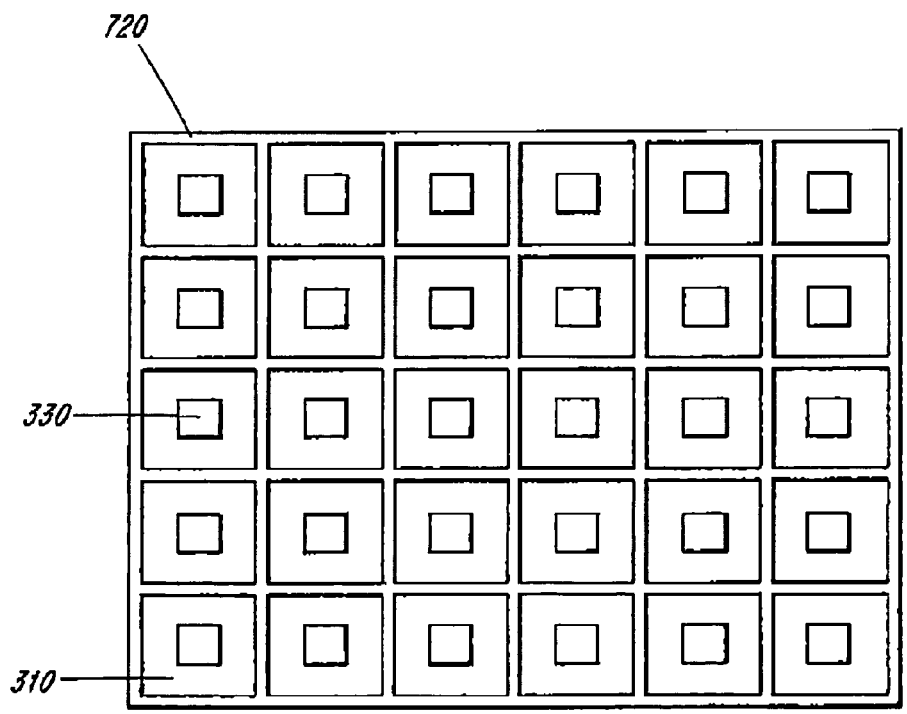
FIG. 7B is a top view of FIG. 7A.
Figure 8A:
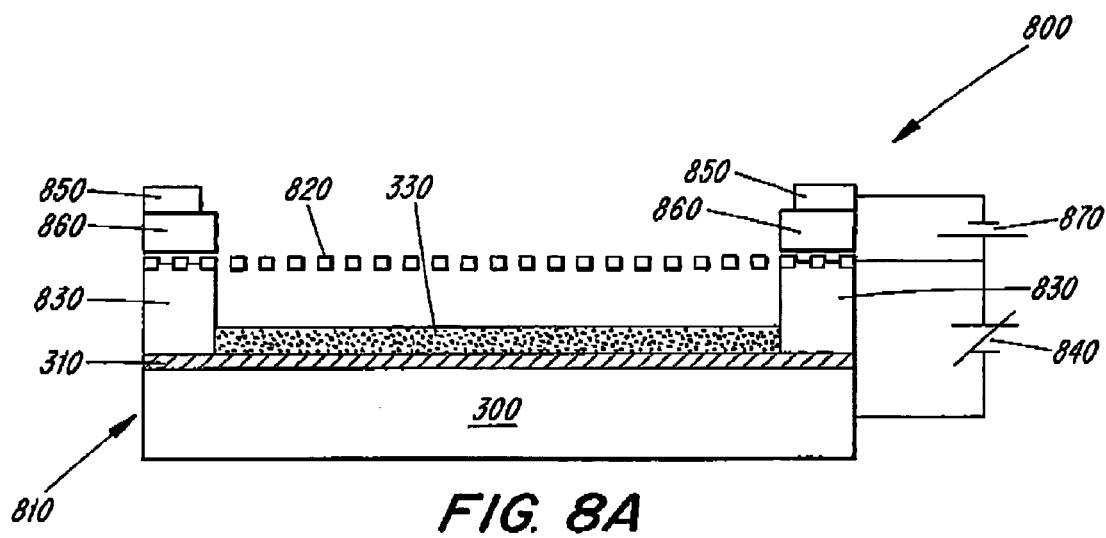
FIG. 8A is a cross-section of a carbon nanotube field emission device according to a further embodiment of the invention.
Figure 8B:
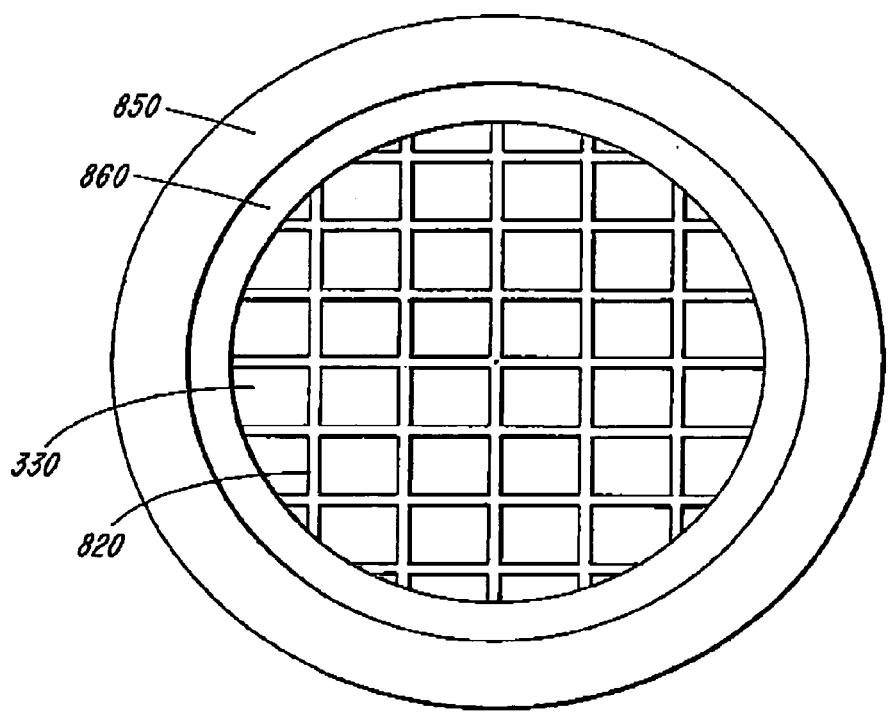
FIG. 8B is a top view of FIG. 8A.

The nanostructure material or single wall carbon nanotubes can be deposited on the substrate 300 with a metal interlayer 310 by a variety of methods, including suspension or solution casting, spraying, spin coating, sputtering, screen printing, or electrophoretic deposition. By way of example, a film having a thickness on the order of 0.01 to 10 μm, and more particularly 0.1 to 1 μm are produced. In another embodiment, a thin and continuous "paper" 350 (FIG. 6) can be applied directly to the substrate. The paper 350 is formed, for example, during the filtration process from precipitation of carbon nanotubes and nanotube bundles on the filtration paper and usually has a smooth surface and is flexible.

Films containing single wall carbon nanotubes formed by other methods such as arc-discharge and chemical vapor deposition can also be formed by the procedures described above. In addition, it is possible to grow carbon nanotube films on substrates directly by the chemical vapor deposition method.

Nanostructure material containing cathode materials of the present invention are characterized by a high emission current density, with a relatively low applied voltage.

Figure 4:
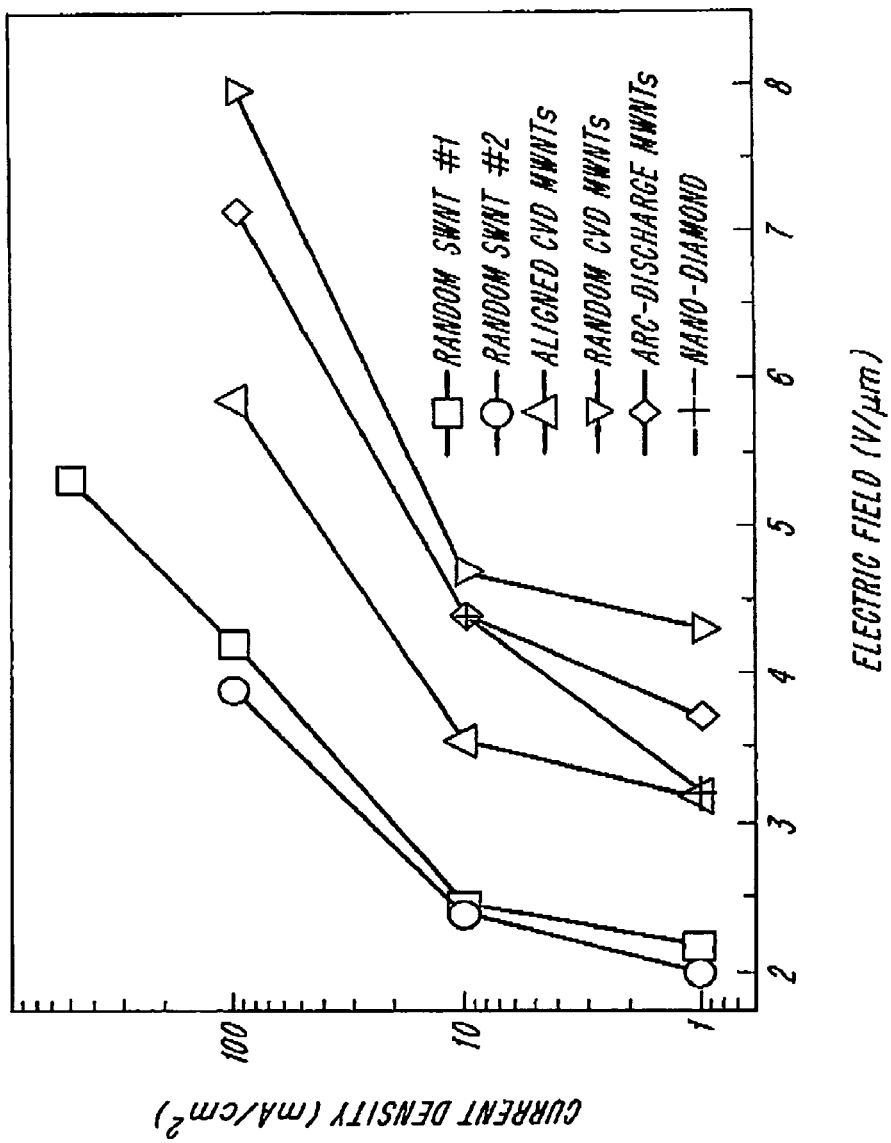
FIG. 4 is a graph depicting the threshold field required to obtain a certain emitted current density for several field emission materials.
Figure 5:
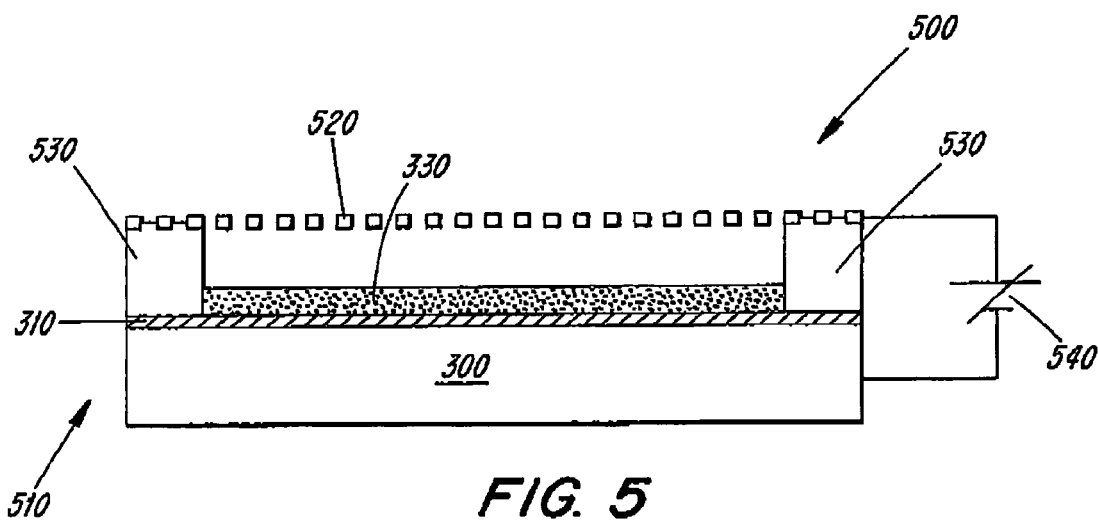
FIG. 5 is a cross-section of a carbon nanotube field emission device according to a first embodiment of the invention.

Field emission measurements have been made on various single wall and multi-wall nanotube materials formed according to the principles of the present invention. FIG. 4 depicts graphically five nanotube materials prepared in accordance with this invention. These measurements show current density of 10 mA/cm$^2$ at an applied electrical field of 2–5 V/μm and 100 mA/cm$^2$ or greater at an applied electrical field of 4–7 V/μm. The results from a nano-diamond field emission material is shown for comparison. As illustrated by FIG. 4, the investigated materials exhibit a relatively high current density under a relatively low applied electrical field voltage.

Table 1 below summarizes the threshold field required to obtain a current density of 10 mA/cm$^2$ for several cathode materials. The carbon nanotubes of the present invention uniformly had a lower threshold field for a given current density than the other materials investigated. In addition, the current density generated was more stable for the carbon nanotube material than for the other materials investigated.

TABLE 1

| Cathode Material | Threshold Field (V/μm) for a current density of 10 mA/cm$^2$ |
| --- | --- |
| Mo tips | 50–100 |
| Si tips | 50–100 |
| p-type diamond | 160 |
| Defective CVD diamond | 30–120 |
| Amorphic diamond | 20–40 |
| Cesium-coated diamond | 20–30 |
| Graphite powders | 10–20 |
| Nano-diamond | 3–5 (unstable > 30 mA/Cm$^2$) |
| Assorted Carbon Nanotubes | 2–5 (stable > 1 A/Cm$^2$) |

Therefore, as evidenced by the above, an x-ray generating device having a cathode comprising a nanostructure materials, such as a single wall nanotube material, according to the present invention is capable of producing an emitted electron current density greater than 100 mA/cm$^2$, preferably 1000 mA/cm$^2$, and most preferably 5000 mA/cm$^2$.

It is contemplated that an electron emitting cathode comprising single walled carbon nanotubes formed consistent with the principles of the present invention may be incorporated into any suitable x-ray generating apparatus. The advantages imparted to such devices enable numerous design modifications to not only the cathode, but to the anode, as well as other components of such x-ray generating devices. A few exemplary devices constructed according to the principles of the present invention are described below.

FIGS. 5–8B depict cross-sections of field emission cathode devices according to the present invention. In one embodiment 500, the field emission cathode structure 510 comprises a nanostructure or carbon nanotube film 330 on a conducting substrate 300, preferably with a desired metal interlayer 310. After deposition, the film 330 is preferably vacuum-annealed. The gate electrode 520, preferably a high melting temperature metal grid, is placed on an insulating spacer 530 which is located between the gate electrode 520 and the nanotube film 330. A power source 540, preferably with variable voltage control, is connected between the gate electrode 520 and the nanotube cathode 510.

In another embodiment 600, the field emission cathode structure 610 comprises a thin nanostructure or carbon nanotube paper 350 placed on a conducting substrate 300 which, preferably, has a desired metal interlayer 310 such as Fe or Ti. The paper 350 is pressed onto the substrate 300 with the metal interlayer 310, and is preferably vacuum-annealed to achieve adhesion. The paper 350 is further fixed on the substrate 300 by an insulating collar 630. A gate electrode 620, preferably a high melting temperature metal grid, is placed on the insulating collar 630. A power source 640, preferably with variable voltage control, is connected between the gate electrode 620 and paper 350 or the conducting substrate 300.

Alternatively, an embodiment 700 may comprise a field emission cathode structure 710 comprising a nanostructure or carbon nanotube film 330 on a conducting substrate 300, preferably with a desired metal interlayer 310, wherein the film 330 is patterned and aligned with the openings in a gate electrode 720 to minimize overheating of the metal grid caused by bombardment with the field emitted electrons. The gate electrode 720, preferably a high melting temperature metal grid, is placed on an insulating spacer 730. The metal grid 720 and the patterned film 330 are placed in an off-set geometry to avoid the problems of overheating of the grid 720 due to field emitted electrons striking the grid 720 for extended periods of time.

In yet another embodiment 800, the field emission cathode structure 810 comprises a nanostructure or carbon nanotube film 330 on a conducting substrate 300, preferably with a desired metal interlayer 310. After deposition, the film 330 is preferably vacuum-annealed. The gate electrode 820, preferably a high melting temperature metal grid, is placed on an insulating spacer 830 which is located between the gate electrode 820 and the nanotube film 330. A power source 840, preferably with variable voltage control, is connected between the gate electrode 820 and the nanotube cathode 810. To improve the stability of the x-ray intensity, a feedback circuit can be incorporated to vary the applied voltage between the gate electrode 820 and cathode 810 accordingly to compensate the fluctuation in the x-ray tube current (electron current reaches the target). For example, a current meter can be included to monitor the x-ray tube current (which controls the x-ray intensity, together the acceleration voltage). If the current drops below the set value, the gate voltage (which controls the field-emitted current density from the cathode) will be increased until the set tube current is reached.

Additionally, the field emission cathode structure 810 may further comprise a focusing ring 850 which allows the emitted electron beam to be focused to a narrow area. The focusing ring 850 is mounted to the structure 810 above the gate electrode 820 and is isolated from the gate electrode by a second spacer 860. The focusing ring is provided with a negative bias 870.

Alternatively, the nanostructure-containing or carbon nanotube material can be deposited on a substrate with a concave surface. The gate electrode is provided with a curvature such that a constant distance between the cathode and the gate electrode is maintained. Such a construction also acts to focus the field emitted electrons toward the target anode.

Figure 9:
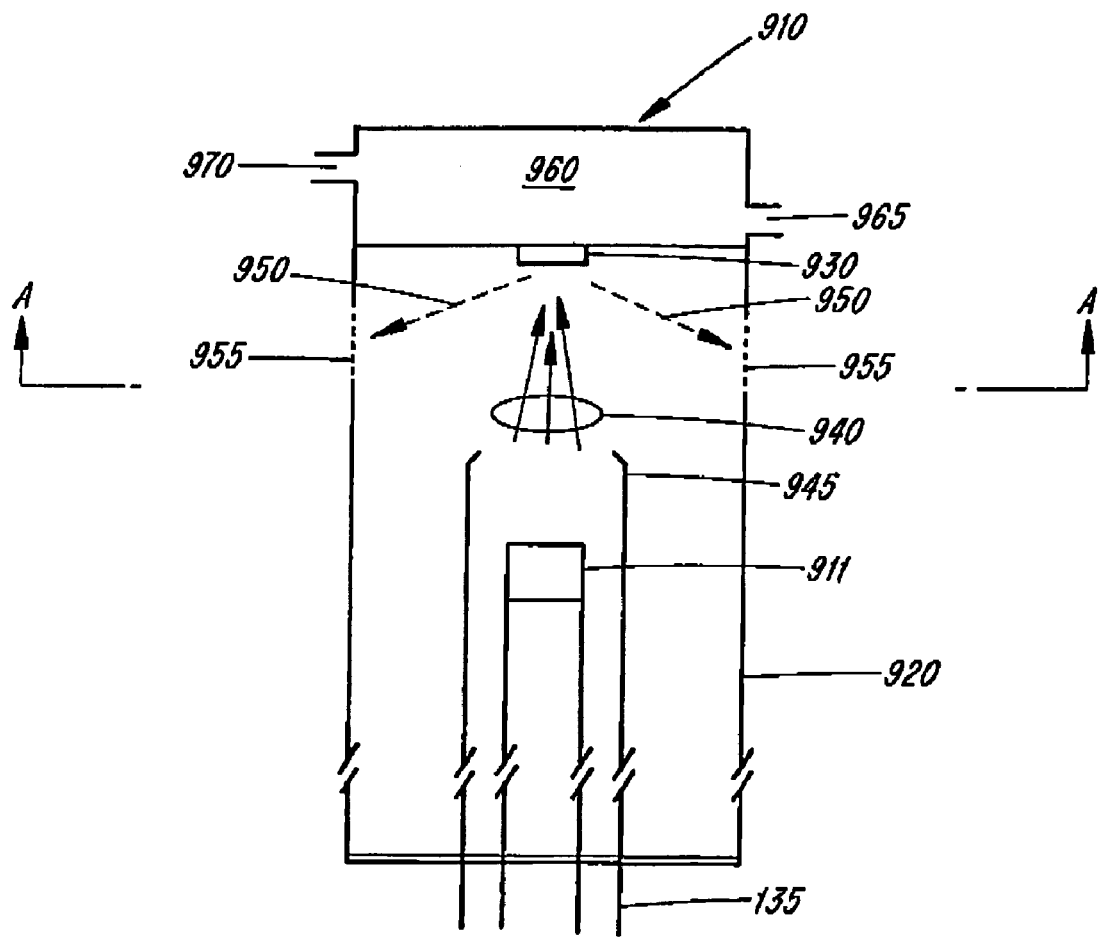
FIG. 9 is a cross-section of a further embodiment of a vacuum x-ray tube with a field emission carbon nanotube cathode.

FIG. 9 is a vacuum x-ray tube with a field emission nanostructure or carbon nanotube cathode according to the present invention. Within the x-ray generating device 910, a field emission cathode device 911 is positioned for use as an electron generating cathode. Attached to the field emission device are electrical leads 935 to supply a control voltage. Under a sufficient field between the carbon nanotube field emission cathode devices 911 and the metal anode target 930, electrons emitted towards the anode 940 first travel through a focusing shield 945. After striking the anode target 930, x-rays 950 are emitted which pass through a window 955 in the side of the vacuum chamber 920. Cooling water is provided in this embodiment through the use of a cooling water chamber 960 with inlet 965 and outlet 970. However, since the field emission cathode device 910 of the present invention can produce an emitted electrode current density of enough intensity to cause x-rays to be emitted from the anode, without relying on thermionic effects, the cooling requirements of the device are greatly reduced. Moreover, the x-rays can be more precisely pulsed by simply varying the control voltage. Mechanical shutters and the like can be eliminated.

Figure 10:
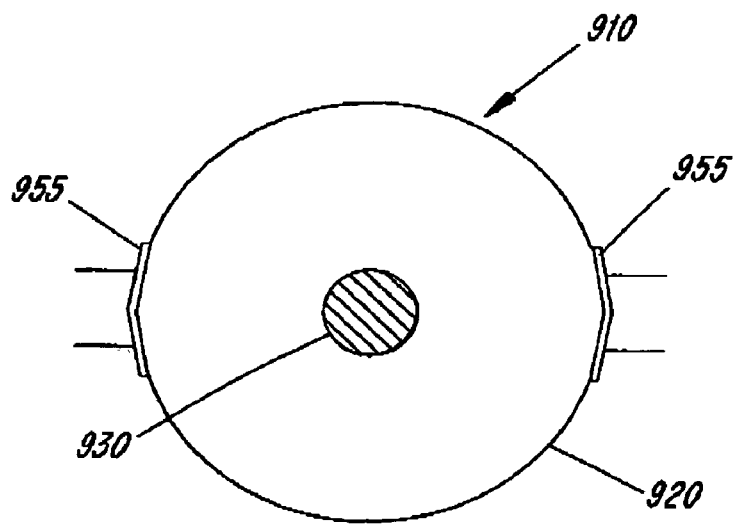
FIG. 10 is a view of the device of FIG. 9 taken at A—A.

FIG. 10 shows a view of the device of FIG. 9 taken along line A—A. In this view, the relative orientation of the anode 930 and the windows 955 may be seen.

Figure 11:
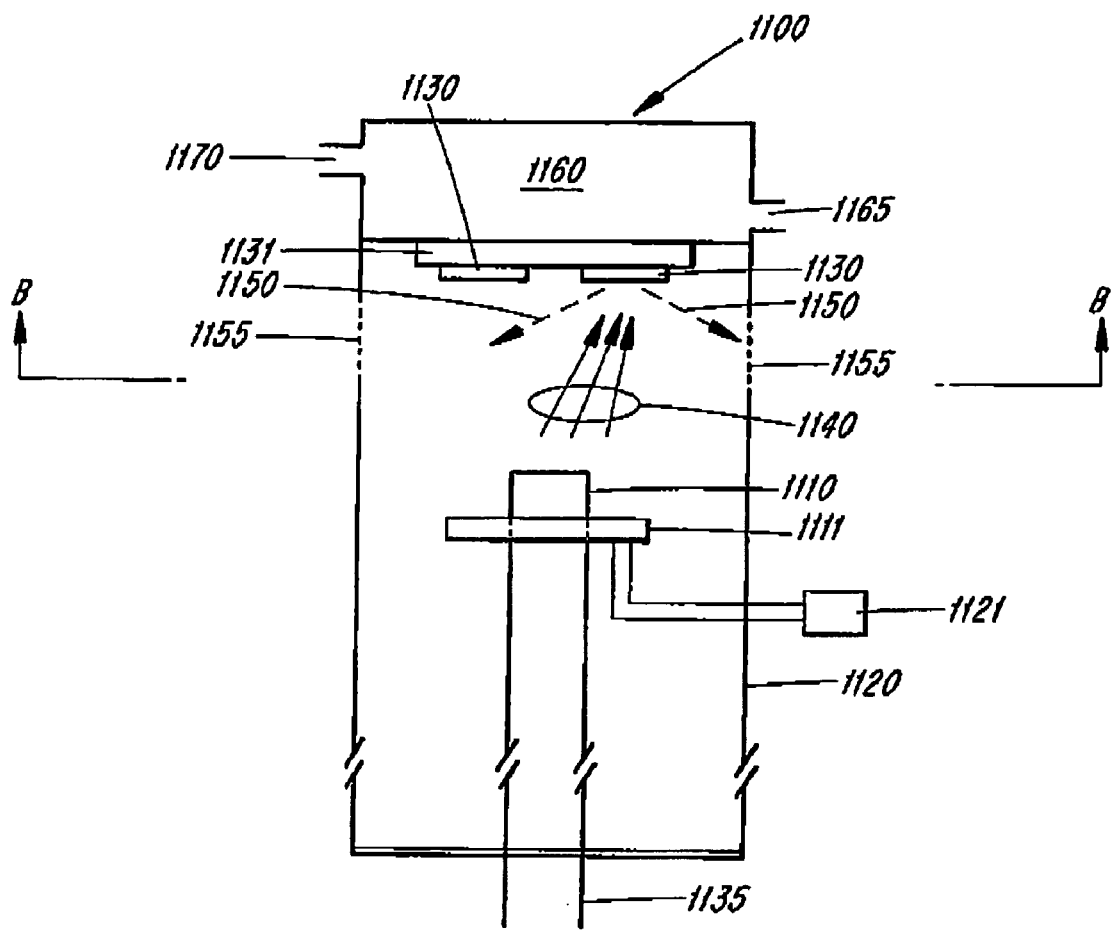
FIG. 11 is a cross-section of a further embodiment of a vacuum x-ray tube with a field emission carbon nanotube cathode.

FIG. 11 is a second embodiment 1100 of a vacuum x-ray tube with a nanostructure or carbon nanotube field emission cathode device 1110 of the present invention. In this embodiment, the field emission cathode devices 1110 are mounted on a translation stage 1111. The translation stage position is controlled by a translation controller 1121. A field may be established between the field emission cathode device 1110 and the anode 1130 by applying current to the cathode leads 1135. Under the field that is formed, electrons 1140 are field emitted from the cathode and are directed towards the anode. The bombardment of the emitted electrons produces x-rays 1150 which travel from the anode target through the windows 1155 in the side of the vacuum chamber 1120. Residual heating of the anode due to the electron bombardment is removed through the use of cooling water or other heat sink. FIG. 11 shows a cooling water chamber 1160 provided with an inlet 1165 and an outlet 1170. In addition, the anode metal target 1130 is mounted on an anode mounting platen 1131. This platen has a high thermal conductivity to allow for rapid removal of heat from the anode by the heat sink. The mounting platen 1131 is affixed to the vacuum chamber at a common surface with the heat sink.

Alternatively, the anode mounting platen 1131 may be mounted so as to provide for rotation about a centerline axis normal to the plane of the platen. This rotation provides for individual and distinct anode metal targets 1130 to be positioned in the path of the beam of emitted electrons 1140. Through the use of this rotation device, x-rays 1150 of multiple characteristic wavelengths corresponding to the composition of the material of the individual anodes may be produced.

In another additional embodiment, the anode mounting platen 1131 may be stationary and the translation stage 1111 controlled by a controller 1120 may provide for an emitted electron beam 1140 which may impinge distinctly each of the anode metal targets.

Alternatively, the translation stage 1111 may have a rasterization capability. Through the use of individual, group, or matrix addressing of selected regions of the field emission cathode device 1110, a rasterized emitted electron beam may be generated and directed as such to impinge distinctly each of the anode metal targets 1130. All of the benefits of previous embodiments being realized through such a construction.

In a further embodiment, the anode is stationary and an array of individually controlled field emission cathodes is incorporated. By selectively turning on and off certain field emitters in the array field emitted electrons will strike different parts of the target anode surface.

In yet another embodiment, the anode mounting platen 1131 is affixed to a movable base or arm. The base or arm may be easily moved within or removed from the vacuum chamber 1120 to facilitate loading and unloading of anode targets by the user.

Figure 12:
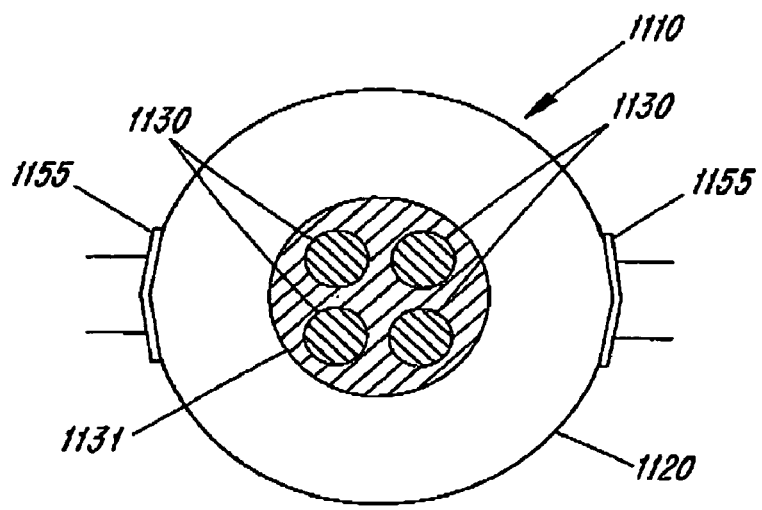
FIG. 12 is a view of the device of FIG. 11 taken at B—B.

FIG. 12 is a view of the device of FIG. 11 taken along line B—B. In this view, the positions of the anode metal targets 1130 on the anode mounting platen 1131 are more clearly shown.

Through the above-described construction, the same benefits of using the field emitting control of the present invention previously discussed in connection with the embodiment of FIG. 9 are realized. In addition, the scanned emitted electron beam can advantageously strike different target materials thereby enabling different types of characteristic x-rays to be produced by the same device. Also, the scanned beam strikes different areas of the same target material, thereby reducing the overall heating of the target.

In certain applications of x-ray generating devices, such as medical applications, important requisite characteristics include precise control over x-ray generation, generation of high intensity x-rays, and a small apparent focus spot of generated x-rays.

Certain conventional x-ray generating devices have dual focus spots with apparent focus spot sizes of the generated x-rays of 0.3 mm$^2$ and 1.00 mm$^2$. For a target angle of 6° and 15°, this translates into an actual area of electron bombardment on the anode of 0.3×3.0 mm$^2$ and 1.0×4.0 mm$^2$. In order to reduce the focus spot, a smaller target angle on a higher emitted electron current from the cathode are needed. This is not possible in conventional devices due to constraints on the power which can be supplied to the cathode filament.

These deficiencies can be overcome by devices of the present invention. A device constructed according to the principles of the present invention, which include a nanostructure-based field emitter are capable of generating an emitted electron beam current which is roughly equivalent to the current supplied to the cathode, thereby enabling anode targets with smaller angles, and a resulting smaller apparent focus spot size.

Figure 13:
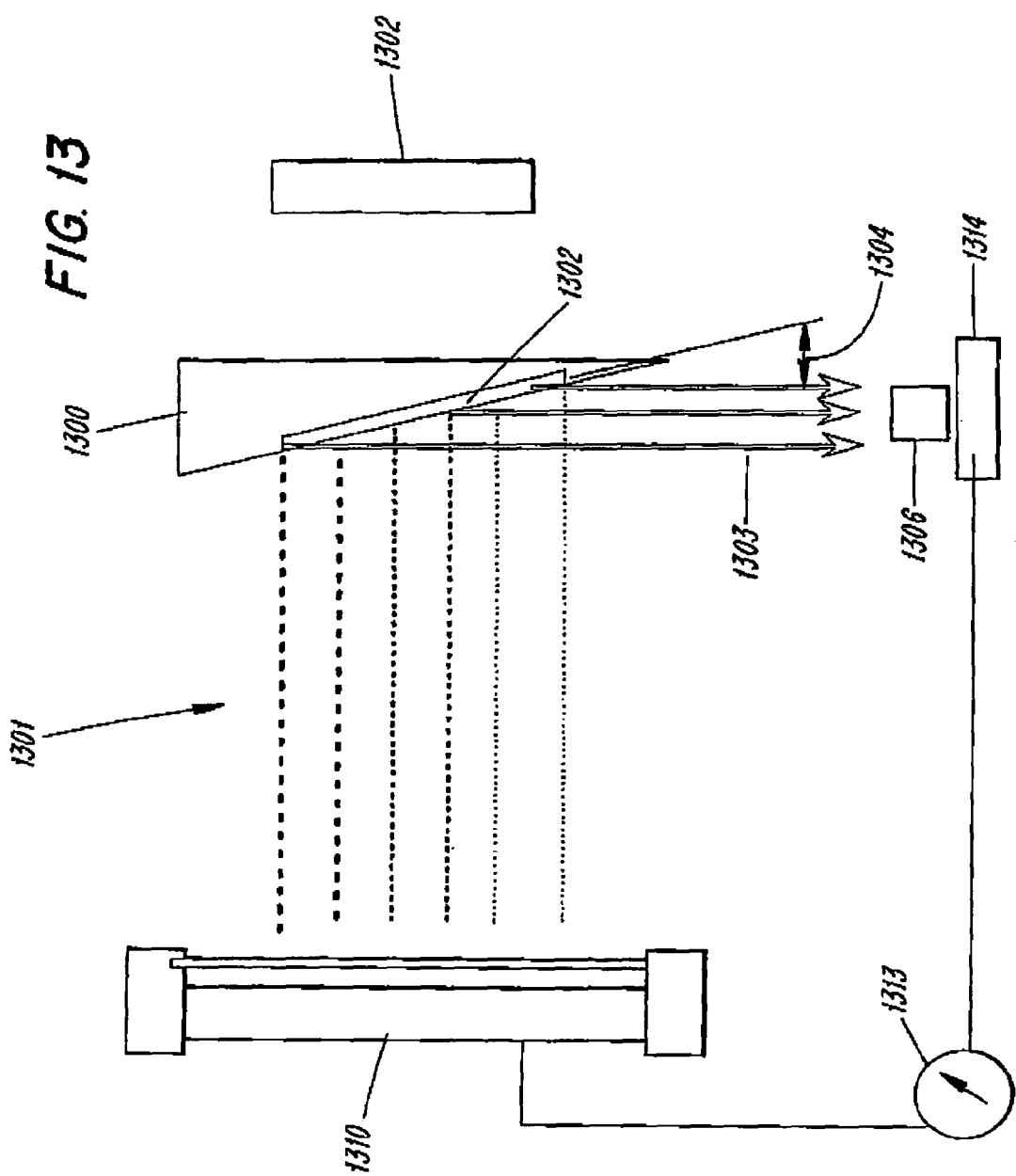
FIG. 13 is a schematic illustration of an anode construction according to the present invention.

One such anode constructed according to the principles of the present invention is illustrated in FIG. 13. An emitted electron beam(s) with a current of 100–5,000 mA is incident upon the focus spot 1302, which is shown in both front view and from the side in FIG. 13. Focus spot 1302 can be 10–30 mm in length and 0.1–0.5 mm in width. According to the invention, the target angle can be reduced to achieve a target angle 1304 of, for example, 2°–10°. In one preferred embodiment, for a dual spot focus construction, the target angle can be about 2° and about 6°. The above-described construction is capable of producing a smaller "apparent" focal spot 1306 having an area of 0.1–0.5 mm$^2$. In one preferred embodiment, for a dual focal spot construction, an apparent focal spot of 0.1 mm$^2$ and 0.3 mm$^2$ are attained.

In applications such as computed tomography, the uniformity of the x-ray fan beam is important. Achieving uniformity in conventional tube design is difficult because emission of x-rays from the target surface is anisotropic (namely, dependent on the emission direction relative to the surface). Different parts of the x-ray beam come from different combinations of emission angles from different parts of the focus area. Thus, even when the focus spot is bombarded with a uniform electron beam, the resulting x-ray beam is non-uniform.

The current inventions allow one to control precisely the current density and distribution of electron beam emitted from nanostructured cathode. This enables a new method of generating an x-ray beam with superior uniformity. An embodiment of such a method is also schematically shown in FIG. 13. By controlling the voltage applied between the nanostructured emitter 1310 and gate 1313, an electron beam 1301 with certain desired current density and distribution can be generated. When striking the anode 1302, the specially designed non-uniform electron beam 1301 can generate an uniform beam of x-ray 1303. A further refinement of the method may include a feed-back controlling mechanism 1313 between x-ray detector 1314 and cathode 1310. Such a mechanism will allow the generation of x-ray beam with certain desired distribution of intensity, which may be of advantage in certain application such as in digital mammography.

The anode construction of the present invention, with its smaller apparent focal spot sizes, leads to dramatic enhancements of imaging resolution and speed compared to conventional devices. For instance, an x-ray generating device constructed according to the principles of the present invention would be capable of producing the same amount of x-rays as current machines, but with 3–4 times better resolution, or with comparable resolution but 3–4 times the intensity of a conventional device.

In certain applications, such as digital fluoroscopy and radiography, an energy subtraction technique is used to enhance the contrast of certain materials in the object(s) being analyzed. This technique involves obtaining a first image using x-rays having a lower average energy, and "subtracting" this first image from a second image obtained using x-rays having a higher average energy. The above technique is conventionally practiced by alternating the voltage applied to the cathode, between a low kV value to produce x-rays of lesser intensity, and a higher kV value to produce x-rays of a higher intensity. Due to the previously described difficulties in the initiation and termination of thermionic electron emissions, this process is slow. When used in medical applications, this causes the patient to be unnecessarily exposed to higher dosages of x-rays.

Due to the ease in which an emitted electron beam produced according to the present invention can be controlled and focused, an anode target comprising multiple target materials can be utilized.

One such device is illustrated in FIG. 14. A multiple target anode 1400 is provided with a first target material 1402 and a second target material 1404. A conical or frustoconical face 1403 is defined by the first and second target materials 1402 and 1404. By way of example, first target material 1402 can be a material which generally produces x-rays with a relatively low average energy, and second target material 1404 can be a material which generally produces x-rays of a relatively higher intensity. Of course, this arrangement can be reversed. A voltage 1406 is applied to a plurality of field emitters 1408 constructed according to the present invention which emit a stream of electrons which strike the target anode 1400. The emitters 1408 can be pulsed or alternated so that the electron stream emitted therefrom alternatively strike the first target material 1402 to produce x-rays with relatively low energy 1410, and the second target material 1404 to produce x-rays with a relatively high energy 1412.

The inventive device is less costly than conventional devices and possesses increased operational speed, which is especially beneficial in applications such as fluoroscopy, radiography, and computed tomography.

A method performed consistent with the present invention includes providing a field emission device, comprising a nanostructure containing material, which is introduced into a chamber into which at least one of a plurality of anode targets has been previously or will be disposed. The field emission device is positioned to act as a cathode in an x-ray generating device. The chamber is subsequently sealed and evacuated to a predetermined minimum pressure, or back-filled with an inert atmosphere, or neither of the above in preparation of generating x-rays.

The construction of the field emission cathode may be by a variety of methods, including those previously described such as laser ablation followed by purification and deposition of carbon nanotubes on a substrate.

Under an applied control voltage, the field emission cathode of the present invention emits a stream of elections. The application of the control voltage determines the initiation and termination of the emission, which thereby is controlled in duration and intensity. Pulsing the electron beam affords the advantage of reduced anode heating, with its attendant benefits, as well as more precise control over the duration of the x-rays emitted. Alternatively, the emitted beam may be pulsed by controlling the applied control voltage.

As yet another alternative, arrays of nanostructure materials may be addressed by the control voltage individually, or in predetermined sequences or groupings to provide control over the emitted electron beam so as to direct the beam to impact any one of the at least one of a plurality of anode targets. By this method, multiple targets made of different material may be impacted in the same device generating a broader spectrum of emitted x-rays without having to add and remove targets of different materials from the chamber. Additionally, this alternative may be used to reduce the time any one area of an anode is bombarded, thus contributing to reduced heating of the anode.

The beam of field emitted electrons which impacts an anode target generates x-rays by means well known in physics. The generated x-rays then exit the chamber through x-ray transparent windows and are available for use in various applications including medical and scientific.

Exemplary embodiments of the present invention allow for independent control of electron emission current and x-ray energy in field emission cold cathode x-ray tubes. Exemplary field emission cold cathode x-ray tubes are described in U.S. patent application Ser. No. 09/679,303 entitled "X-ray Generating Mechanism Using Electron Field Emission Cathode." This patent application describes a field emission nano structure cathode material for use in an x-ray generating device. The nano structure field emission material is capable of producing, in a controlled and reliable manner, a high emitted electron current density through the application of a relatively small control electrical field. Accordingly, a substantially higher electron beam current can be achieved compared with that of thermionic emission. The nano structure field emission cathode is capable of providing precise step-function initiation and termination of the emission of electrons in a pulse varying duration simply by varying the applied voltage. Using the x-ray tubes with nano structure based field-emission cathodes of this application, it is possible to construct portable x-ray machines for use in the field. For more information regarding these structures, the interested reader should refer to International Publication No. 02/31857A1, which corresponds to the '303 application, the entire disclosure of which is herein expressly incorporated by reference. Although the following describes the use of such field emission cold cathode x-ray tubes in connection with the present invention, one skilled in the art will recognize that methods and apparatus described herein are equally applicable to other types of structures.

Figure 15A:
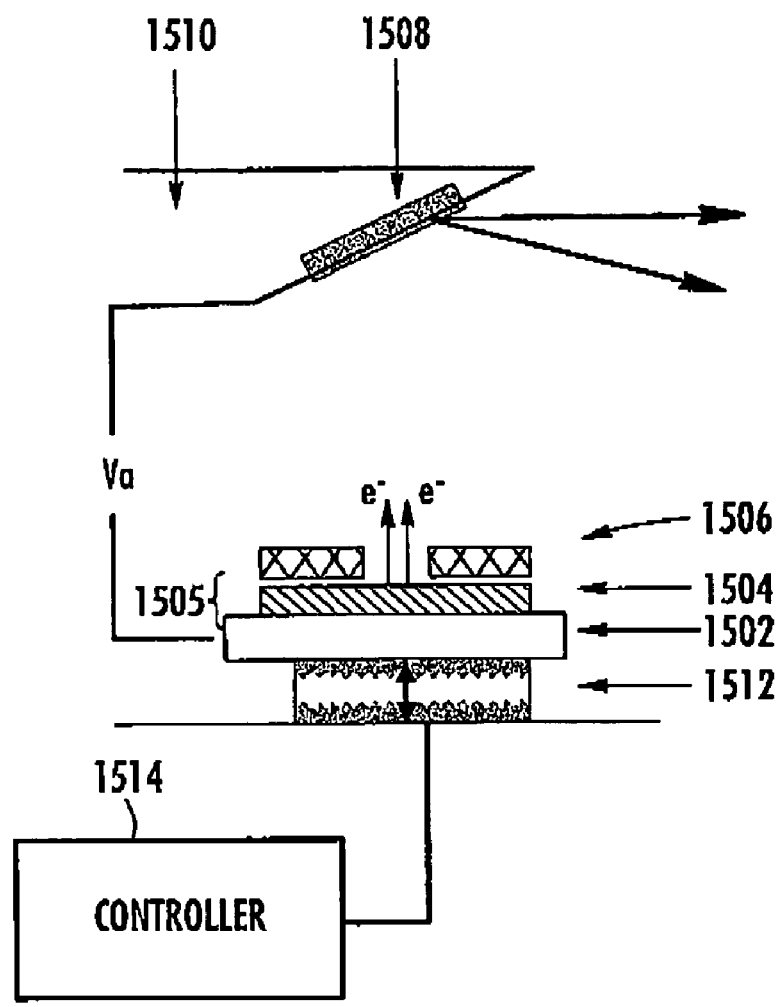

FIGS. 15a through 15d illustrate an x-ray tube in accordance with a first embodiment of the present invention. In accordance with the first embodiment of the present invention, the electron emission current is controlled by adjusting the distance between the anode and the cathode. FIG. 15a illustrates a cathode 1505 comprising a substrate 1502 and a field emissive material 1504. The field emission cathode 1505 can be a layer of 1-dimensional (1D) nano-objects such as nanotubes and nano wires deposited on a metal substrate 1502. The 1D nano-objects can consist of at least one of the following elements: carbon, nitrogen, boron, oxygen, Si, Ge, Ga, In, metals, carbide, nitrides, carbides, and oxides. Mounted on the field emissive material 1504 is a focus ring 1506 for focusing the emissions from the field emissive materials 1504 onto anode 1508. Anode 1508 is mounted on support 1510. Underneath the substrate 1502 is a piezoelectric material 1512. The piezoelectric material 1512 receives electrical energy from controller 1514. The electrical connection between controller 1514 (located outside the x-ray tube) and the piezoelectric material 1512 (inside the x-ray tube) is made through the use of a vacuum feed-through. One of ordinary skill in the art recognizes how to make and use a vacuum feed-through, and hence, a detailed description of this structure is omitted.

In accordance with the first embodiment of the present invention, a voltage $V_a$ is established between cathode 1505 and anode 1508. For a given voltage V and a distance D between the anode and the cathode, the applied electric field, i.e., the x-ray energy, is E=V/D. In electron field emission the electron emission current I is related to the applied electric field E through the Fowler-Nordheim equation as follows:

$$J = aE^2 \exp(-b\phi^{3/2}/E)$$

where J is the emitted electron current, $\phi$ is the work function of the field emission materials, E is the applied electric field, and a and b are Fowler-Nordheim parameters which are dependent upon the particular setup geometry and nanostructures of the emissive materials. One of ordinary skill in the art knowing the particular setup geometry and the nanostructure of the emissive materials can readily determine a and b.

Accordingly, it can be seen that the electric field E is proportional to the voltage applied between the cathode and anode ($V_a$), and inversely proportional to the distance (D) between them.

In accordance with the first embodiment of the present invention, the relative position between the anode and the cathode are selected to correspond to a distance which will produce the most frequently used electron beam current in the most commonly used x-ray emission energy for a particular application setting of the x-ray tube. The voltage $V_a$ is selected to produce the desired x-ray radiation, and the location of the cathode is adjusted to achieve the desired electron beam current. Accordingly, the total emission current increases when the distance (D) between the anode and the cathode is reduced, and decreases when the distance (D) between the anode and the cathode increases. In accordance with exemplary embodiments of the present invention controller 1514 is constructed such that the operator of the x-ray device can set the desired electron beam current, and the device will automatically adjust the cathode-anode distance.

Figure 15B:
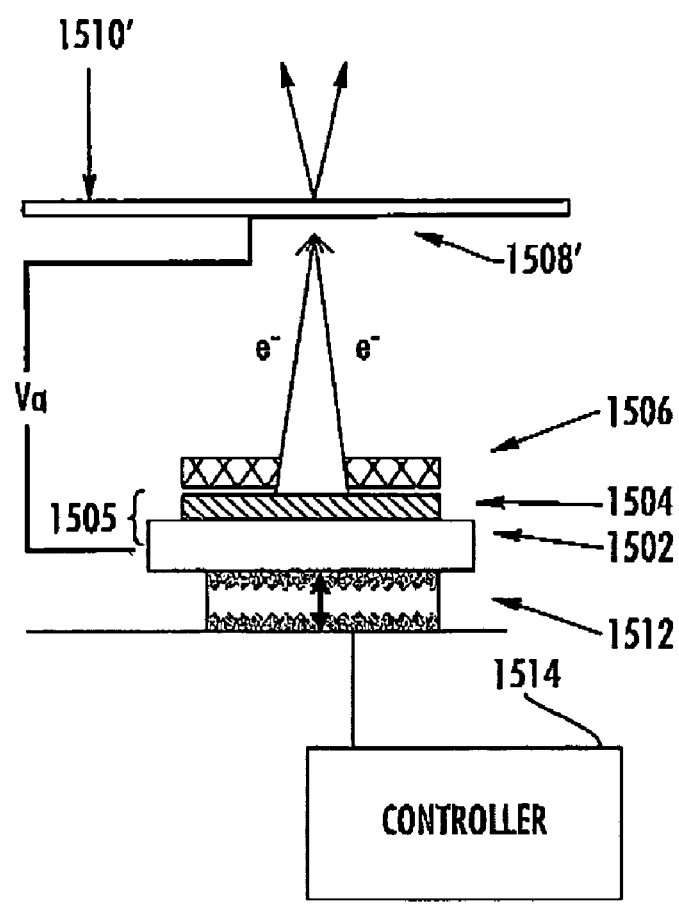

FIG. 15*b* illustrates a second arrangement in accordance with the first embodiment of the present invention. In both FIGS. 15*a* and 15*b* the x-ray generating target material is mounted on the support. In FIG. 15*a*, the generated x-ray radiates away from the support, whereas in FIG. 15*b* the x-ray radiates through the support.

Figure 15C:
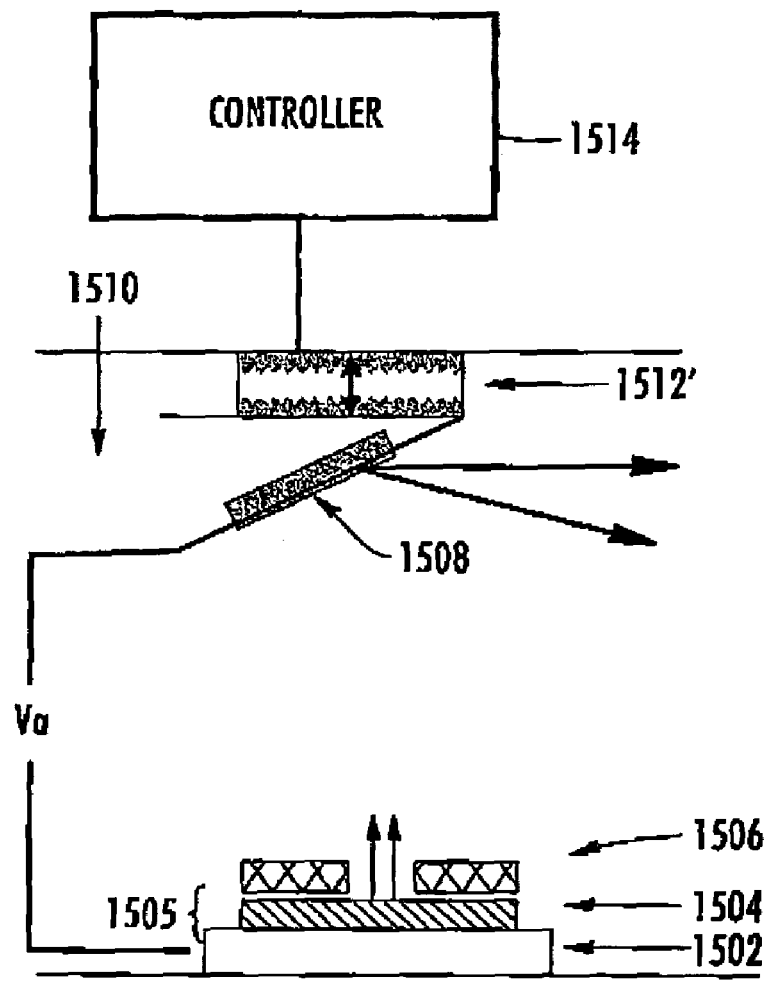

FIG. 15*c* illustrates a third arrangement in accordance with the first embodiment of the present invention. In FIG. 15*c*, piezoelectric material 1512' is mounted on anode support 1510. In accordance with this arrangement, the cathode 1505 is stationary and the anode 1508 is moved relative to the cathode by the application of electricity by controller 1514 to piezoelectric material 1512'.

Figure 15D:
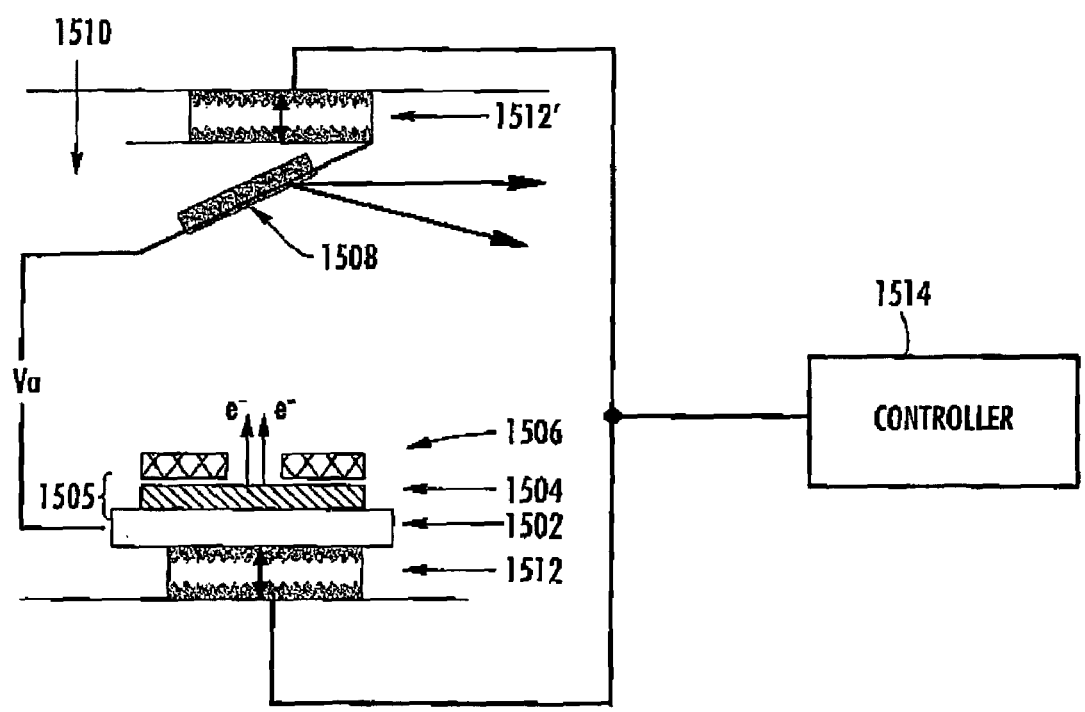

FIG. 15*d* illustrates a fourth arrangement in accordance with the first embodiment of the present invention. As illustrated in FIG. 15*d*, piezoelectric material is mounted to the support 1510 of anode 1508 and to cathode 1505. Accordingly, the distance between the anode 1508 and cathode 1505 is adjusted by applying electricity to piezoelectric material 1512 and/or piezoelectric material 1512'.

In another arrangement in accordance with the first embodiment of the present invention, either the anode or the cathode is mounted on a translation stage that enables translational motion to adjust the distance between the cathode and the anode. Translation stages being well known in the art, one of ordinary skill in the art will recognize how to make and use a translation stage in connection with the present invention for mechanical adjustment of the distance between the cathode and the anode.

FIGS. 16*a* and 16*b* illustrate a second embodiment of the present invention. In accordance with the second embodiment of the present invention, the temperature of the cathode is controlled to adjust the electron emission current. Specifically, the higher the temperature of the cathode 1505, the higher electron emission current. Accordingly, controller 1514 is connected via a vacuum electrical feed-through to electric heater 1516. By controlling heater 1516, the electron emission current from cathode 1505 can be controlled independently of the voltage $V_a$. The heater 1516 can be made of metal filaments in a ceramic housing or other similar structures. Similar to the first embodiment of the present invention, controller 1514 is designed such that an operator need only enter the desired electron emission current and the controller will adjust the heater 1516 accordingly.

FIG. 17 is a graph illustrating the electron emission current as a function of the temperature for two different applied electrical fields. As can be seen from the curves in FIG. 17, to control the emission current, the temperature of the cathode should be increased to above 500° C. More particularly, as illustrated in FIG. 17, to achieve meaningful control over the current, the cathode should be heated above 400° C. Heating the cathode to lower temperatures, e.g., 100° C., provides minimal change in the current density, and hence, provides little, if any, control over the current.

FIGS. 18*a* through 18*c* illustrate the third embodiment of the present invention. In accordance with the third embodiment of the present invention, the electron emission current and x-ray energy are independently controlled by optical excitation of the field emission materials by shining an optical light source on the cathode. In accordance with the third embodiment of the present invention, the field emission cathode 1504' can be a layer of nanotubes deposit on metal substrate 1502, wherein the nanotubes comprise at least one of the following element C, N, B, and O, or a layer of nano rods. As illustrated in FIG. 18*a*, controller 1514" controls photon source 1816 for emitting photons on emissive material 1504'. In accordance with the third embodiment, the controller 1514 is external to the vacuum tube, whereas the photon source 1816 can be either internal or external to the vacuum tube. If photon source 1816 is external to the vacuum tube, the photon source emits photons onto the emissive material 1504' via an optical window.

In accordance with the third embodiment of the present invention, the voltage $V_a$ is increased to a value just below the threshold voltage for field emission from the cathode 1505'. At this point no electrons are emitted from the cathode, and hence, no x-ray radiation is produced. The photon source is then turned on which causes a bombardment of the electron emissive material by photons. The electrons in the emissive material 1504' are excited to high energy states due to the excitement of the incident photons. The excited electrons tunnel through the energy barrier and field emit. The emitted electrons are accelerated by the electrical field between the anode and the cathode 1505' and bombard on the anode (not illustrated). X-ray radiation is then emitted from the anode (not illustrated). Accordingly, the field emitted electron current, and therefore the intensity of the x-ray radiation generated, can be varied without changing the acceleration voltage $V_a$, by varying the intensity of the incident photons.

FIGS. 18*b* and 18*c* illustrate a second aspect of the third embodiment of the present invention. In accordance with this aspect, the field emission cathode 1505' can comprise multiple emitters. Again, a voltage is established between the cathode and anode such that the electrical field is just below the threshold for emission. A focused photon beam is scanned across the surface of the cathode 1505'. The flux, i.e., number of photons per unit area per unit time, and the energy per photon is adjusted such that the area on the cathode that is bombarded by the photons field emit electrons whereas the rest of the cathode does not. This provides a convenient technique for addressable emission from the individual emitters or groups of emitters on the cathode surface. By scanning the beam across the cathode surface, an array or matrix of electron beams can be generated from the cathode, and as a result, an array or a matrix of x-ray beams can be produced using such a system.

The present invention has been described above in connection with x-ray radiation systems to illustrate the advantageous aspects thereof. Such a description should not be limiting on the present invention. Specifically, the present invention is equally applicable to instruments and devices which employ electrons other types of radiation, such as gamma ray radiation, ultraviolet ray radiation, or visible light radiation. Such instruments and devices include, but are not limited to, field emission displays, microwave tubes, electron beam lithography, electron soldering machines, plasma ignition sparks, transmission electron microscope (TEM), scanning electron microscope (SEM), and other electron spectroscopy instruments. Moreover, those of ordinary skill in the art will recognize that the present invention can be practiced in any type of device where electron beams are generated by field emission with applications of electric voltage between field emissive materials (cathodes) and targets (anodes).

Variations of the above-described exemplary method, as well as additional methods, are evident in light of the above-described devices of the present invention.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

The present invention has been described with reference to several exemplary embodiments. However, it will be readily apparent to those skilled in the art that it is possible to embody the invention in specific forms other than those of the exemplary embodiments described above. This may be done without departing from the spirit of the invention. These exemplary embodiments are merely illustrative and should not be considered restrictive in any way. The scope of the invention is provided by the appended claims, rather than the preceding description, and all variations and equivalents which fall within the range of the claims are intended to be embraced therein.

What is claimed is:

1. An electron beam current generating apparatus comprising:
 a field emission cathode;
 an anode; and
 a controller which independently controls an emission current from the field emission cathode and electron energy striking the anode by controlling a voltage applied between the field emission cathode and anode, and by controlling one of a temperature of the field emission cathode to a temperature above 400° Celsius and a shining of photons on the field emission cathode, wherein the field emission cathode includes carbon nanotubes.

2. The electron beam current generating apparatus of claim 1, wherein high energy electrons bombard the anode, thereby generating radiation from the anode.

3. The electron beam current generating apparatus of claim 2, wherein the radiation is gamma ray radiation, x-ray radiation, or ultraviolet ray radiation.

4. The electron beam current generating apparatus of claim 2, wherein radiation flux and radiation energy are controlled by said electron beam current and the electron energy.

5. The electron beam current generating apparatus of claim 1, further comprising:
 a distance adjuster, controlled by the controller, to adjust a distance between the field emission cathode and the anode.

6. The electron beam current generating apparatus of claim 5, wherein the distance adjuster mechanically adjusts the distance.

7. The electron beam current generating apparatus of claim 5, wherein the distance adjuster electrically adjusts the distance.

8. The electron beam current generating apparatus of claim 7, wherein the distance adjuster is a piezoelectric material.

9. The electron beam current generating apparatus of claim 8, wherein the piezoelectric material is connected to the anode.

10. The electron beam current generating apparatus of claim 8, wherein the piezoelectric material is connected to the field emission cathode.

11. The electron beam current generating apparatus of claim 5, wherein the distance adjuster is a piezoelectric material connected to the anode and the field emission cathode.

12. The electron beam current generating apparatus of claim 1, further comprising:
 a temperature control element, controlled by the controller, to adjust a temperature of the field emission cathode to a predetermined temperature above 400° Celsius.

13. The electron beam current generating apparatus of claim 12, wherein the temperature control element is an electrical heater connected to the field emission cathode.

14. The electron beam current generating apparatus of claim 1, further comprising:
 a photon source, controlled by the controller, to shine photons on the field emission cathode.

15. The electron beam current generating apparatus of claim 1, wherein the carbon nanotubes are coated on the field emission cathode.

16. An electron beam current generating apparatus comprising:
 a field emission cathode;
 an anode; and
 means for independently controlling an emission current from the field emission cathode and electron energy striking the anode by controlling a voltage applied between the field emission cathode and anode, and by controlling one of a temperature of the field emission cathode to a temperature above 400° Celsius and a shining of photons on the field emission cathode, wherein the field emission cathode includes carbon nanotubes.

17. The electron beam current generating apparatus of claim 16, wherein high energy electrons bombard the anode, thereby generating radiation from the anode.

18. The electron beam current generating apparatus of claim 17, wherein the radiation is gamma ray radiation, x-ray radiation, or ultraviolet ray radiation.

19. The electron beam current generating apparatus of claim 17, wherein radiation flux and radiation energy are controlled by said electron beam current and the electron energy.

20. The electron beam current generating apparatus of claim 16, further comprising:
means for adjusting a distance between the field emission cathode and the anode, wherein the means for adjusting is controlled by the means for controlling.

21. The electron beam current generating apparatus of claim 16, further comprising:
means for adjusting a temperature of the field emission cathode to a predetermined temperature above 400° Celsius, wherein the means for adjusting is controlled by the means for controlling.

22. The electron beam current generating apparatus of claim 16, further comprising:
means for optical excitation of the field emission cathode by shining of photons on the field emission cathode, wherein the means for optical excitation is controlled by the means for controlling.

23. The electron beam current generating apparatus of claim 16, wherein the carbon nanotubes are coated on the field emission cathode.

24. A method for generating electron beam current comprising:
providing a field emission cathode;
providing an anode; and
independently controlling an emission current from the field emission cathode and a radiation energy between the field emission cathode and anode by controlling a voltage applied between the field emission cathode and anode, and by controlling one of a temperature of the field emission cathode to a temperature above 400° Celsius and shining of photons on the field emission cathode,
wherein the field emission cathode includes carbon nanotubes.

25. The method for generating electron beam current of claim 24, comprising adjusting a distance between the field emission cathode and the anode to control the emission current and the x-ray energy.

26. The method for generating electron beam current of claim 24, wherein the distance is adjusted by a distance adjuster including a piezoelectric material connected to the anode.

27. The method for generating electron beam current of claim 24, wherein the distance is adjusted by a distance adjuster including a piezoelectric material connected to the field emission cathode.

28. The method for generating electron beam current of claim 24, wherein the carbon nanotubes are coated on the field emission cathode.

* * * * *

UNITED STATES PATENT AND TRADEMARK OFFICE
CERTIFICATE OF CORRECTION

PATENT NO. : 7,085,351 B2 Page 1 of 1
APPLICATION NO. : 10/358160
DATED : August 1, 2006
INVENTOR(S) : Lu et al.

It is certified that error appears in the above-identified patent and that said Letters Patent is hereby corrected as shown below:

On the Title page, item (75) Inventors should read:

Jianping Lu; Otto Zhou; Yuan Cheng, all of Chapel Hill, NC.

Signed and Sealed this

Twenty-first Day of November, 2006

JON W. DUDAS
*Director of the United States Patent and Trademark Office*